(12) United States Patent
Quist et al.

(10) Patent No.: US 12,714,290 B2
(45) Date of Patent: Aug. 25, 2026

(54) SYSTEMS AND METHODS FOR CALIBRATING AN ENDOSCOPIC OPTIC SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Brian William Quist, Salem, NH (US); Nathan Anil Netravali, Littleton, MA (US); Matthew Michael Julian, Pittsburgh, PA (US); Gibeom Lee, Pittsburgh, PA (US); João Pedro de Almeida Barreto, Coimbra (PT); Rui Jorge Melo Teixeira, Tondela (PT); Nathan Zamarripa, Kittery Point, ME (US); Philip A. Cormier, Newburyport, MA (US); Rafal Z. Jezierski, Candia, NH (US); Luis Carlos Fial Teixeira Ribeiro, Coimbra (PT); Michael David Bridgers, Andover, MA (US); Craig Anthony Di Stefano, Andover, MA (US); Ashley Brady, Somerville, MA (US); John Anastasiadis, Andover, MA (US); Richard Alexander Del Rio, Andover, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(*) Notice: Subject to any disclaimer, the term of this patent is extended or adjusted under 35 U.S.C. 154(b) by 283 days.

(21) Appl. No.: 18/291,155

(22) PCT Filed: Aug. 29, 2022

(86) PCT No.: PCT/US2022/041845
§ 371 (c)(1),
(2) Date: Jan. 22, 2024

(87) PCT Pub. No.: WO2023/034194
PCT Pub. Date: Mar. 9, 2023

(65) Prior Publication Data

US 2024/0358224 A1 Oct. 31, 2024

Related U.S. Application Data

(60) Provisional application No. 63/239,006, filed on Aug. 31, 2021, provisional application No. 63/239,018, filed on Aug. 31, 2021.

(51) Int. Cl.
*A61B 1/00* (2006.01)
*A61B 1/317* (2006.01)

(52) U.S. Cl.
CPC .... *A61B 1/00057* (2013.01); *A61B 1/000095* (2022.02); *A61B 1/317* (2013.01); *A61B 1/00131* (2013.01)

(58) Field of Classification Search
CPC .......... A61B 1/00057; A61B 1/000095; A61B 1/317; A61B 1/00131; A61B 1/00137
See application file for complete search history.

(56) References Cited

U.S. PATENT DOCUMENTS 5,966,210 A * 10/1999 Rosow ............... A61B 1/00165 356/213
6,361,490 B1 * 3/2002 Irion ...................... A61N 5/062 600/175

(Continued)

FOREIGN PATENT DOCUMENTS

AU 2016315939 A1 4/2018
CN 105976427 A 9/2016

(Continued)

OTHER PUBLICATIONS

International Search Report and Written Opinion mailed Jan. 23, 2023 for International Application No. PCT/US2022/041845, 16 pages.

*Primary Examiner* — John P Leubecker
(74) *Attorney, Agent, or Firm* — Dickinson Wright PLLC

(57) ABSTRACT

Ligament repair. Some examples are directed to methods and related systems for calibration of optical equipment for use in a computer-guided endoscopic ligament repair, such as repair of an anterior cruciate ligament (ACL). Other examples are directed to methods and related systems verification of registration between three-dimensional bone models and bone visible through an endoscope during ligament repair. Yet still further examples are directed to intraoperative changes to the tunnel plans for ligament repair.

17 Claims, 22 Drawing Sheets

(56) References Cited

U.S. PATENT DOCUMENTS 6,388,742 B1* 5/2002 Duckett ................ G01M 11/30 356/73.1
6,833,912 B2* 12/2004 Lei ........................ G01M 11/00 356/243.1
8,223,193 B2 7/2012 Zhao et al.
8,553,965 B2 10/2013 Zhao et al.
8,682,049 B2 3/2014 Zhao et al.
8,758,223 B1* 6/2014 Bodor ................ A61B 1/00057 356/73.1
8,799,221 B2 8/2014 Canessa et al.
9,937,011 B2 4/2018 Yosibash et al.
10,092,361 B2 10/2018 Ferro et al.
10,140,421 B1 11/2018 Bernard et al.
10,269,114 B2 4/2019 Reicher et al.
10,452,813 B2 10/2019 Sorenson et al.
10,499,996 B2 12/2019 De Almeida Barreto
10,603,111 B2 3/2020 Seo
10,645,255 B2 5/2020 De Paepe et al.
10,925,687 B2 2/2021 Sela et al.
10,945,848 B2 3/2021 Unis et al.
2002/0077677 A1* 6/2002 Beck .................. A61B 1/00057 607/88
2002/0120180 A1* 8/2002 Speier ................ A61B 1/00142 600/125
2005/0049457 A1* 3/2005 Leiner ................ G01M 11/0214 600/101
2005/0203384 A1 9/2005 Sati et al.
2005/0261551 A1* 11/2005 Couvillon .......... A61B 1/00059 600/109
2006/0173858 A1 8/2006 Cantlin et al.
2011/0140003 A1* 6/2011 Beck .................. A61B 1/00057 250/459.1
2011/0149057 A1* 6/2011 Beck .................. G01N 21/6456 348/E7.085
2013/0085329 A1* 4/2013 Morrissette ........ A61B 1/00057 600/111
2014/0142422 A1 5/2014 Manzke et al.
2014/0246563 A1* 9/2014 McCaffrey ......... A61B 1/00131 250/208.1
2014/0303990 A1 10/2014 Schoenefeld et al.
2015/0018645 A1 1/2015 Farkas et al.
2016/0015247 A1* 1/2016 Irion .................... A61B 1/0661 600/109
2016/0143511 A1* 5/2016 Cheng .................... A61B 1/126 600/125
2016/0183805 A1 6/2016 Kobayashi et al.
2018/0007346 A1* 1/2018 Ushijima ........... A61B 1/00112
2018/0268110 A1 9/2018 Huynh
2018/0285524 A1 10/2018 Ishikawa et al.
2019/0038365 A1 2/2019 Soper et al.
2019/0206569 A1 7/2019 Shelton, IV et al.
2019/0298154 A1 10/2019 Mach et al.
2020/0019823 A1 1/2020 Wang
2020/0037878 A1 2/2020 Douglas et al.
2020/0082930 A1 3/2020 De Francesco et al.
2020/0170802 A1 6/2020 Casey
2020/0234809 A1 7/2020 Huynh
2020/0357118 A1 11/2020 Yao et al.
2021/0110605 A1 4/2021 Haslam et al.
2021/0110901 A1 4/2021 Cronin et al.
2021/0145254 A1* 5/2021 Shekhar ............. G02B 23/2453
2021/0174920 A1 6/2021 Fan
2023/0190136 A1 6/2023 Kumar et al.
2023/0200625 A1 6/2023 Kumar et al.
2023/0245753 A1 8/2023 Kumar et al.
2023/0263573 A1 8/2023 Bakhishev et al.

FOREIGN PATENT DOCUMENTS

CN 110718284 A 1/2020
CN 108135447 B 3/2021
WO 2007070831 A2 6/2007
WO 2008052283 A1 5/2008
WO 2012096102 A1 7/2012
WO 2020129034 A1 6/2020
WO 2020144483 A1 7/2020
WO 2021067624 A1 4/2021
WO 2021071988 A1 4/2021
WO 2021211516 A1 10/2021
WO 2021211524 A1 10/2021
WO 2021211603 A1 10/2021
WO 2021263174 A1 12/2021
WO 2023043964 A1 3/2023
WO 2023044507 A1 3/2023
WO 2024098058 A1 5/2024

* cited by examiner 400
402
404
406
408
410
412
414
416
418
422
424
426
428

614
616
622
704
600
620
702
706
700
624

SYSTEMS AND METHODS FOR CALIBRATING AN ENDOSCOPIC OPTIC SYSTEM

CROSS-REFERENCE TO RELATED APPLICATIONS

This application is a U.S. National Phase Entry of PCT Application Serial No. PCT/US2022/041845 filed Aug. 29, 2022 and titled "METHODS AND SYSTEMS OF LIGAMENT REPAIR". The PCT application claims the benefit of U.S. Provisional Application 63/239,006 filed Aug. 31, 2021 titled "Methods and Systems of Ligament Repair" and also U.S. Provisional Application 63/239,018 filed Aug. 31, 2021 titled "Video Based Navigation Calibration Apparatus." All of the applications are incorporated herein by reference as if reproduced in full below.

BACKGROUND

The anterior cruciate ligament (ACL) serves as the primary mechanical restraint in the knee to resist anterior translation of the tibia relative to the femur. Similarly, the posterior cruciate ligament (PCL) serves as a mechanical restraint to resist posterior translation of the tibia relative to the femur. These cruciate ligaments contribute significantly to knee stability, and ACL injury is quite common. Most ACL injuries are complete tears of the ligament.

As ACL injuries occur often in patients that are young and active, reconstruction of the ACL is performed to enable a return to activity. The goal is to restore stability of the knee and reduce the chances of further damage to the meniscus and articular cartilage that may lead to degenerative osteoarthritis. Reconstruction may consist of placement of a substitute graft (e.g., autograft from either the central third of the patellar tendon or the hamstring tendons). The ends of the graft are placed into respective tunnels prepared through the femur and the tibia. The ends of the graft may be attached using interference screws or a suspensory fixation device like the ENDOBUTTON™ brand fixation devices manufactured by Smith & Nephew of Andover, Massachusetts, USA.

One challenge in ACL reconstruction is where the tunnels should be placed. The native ACL consists of 2 major bundles—the anteromedial (AM) and the posterolateral (PL) bundle. Often, the goal of the surgery is to place the reconstruction in an anatomical location, for example, placing a single tunnel within the footprint of the native ACL attachment site. In other cases, reconstruction may involve creating two tunnels in both the femur and tibia in an attempt to recreate the two native bundles.

There is considerable variability in the placement of tunnels relative to the planned-tunnel locations. It has been shown that relative to the planned-tunnel location, the errors in actual-tunnel location may vary from 8.3 to 13.9 millimeters (mm). Further, the failure rate in ACL reconstructions ranges from 10-15%, with 61% of the failures attributable to technical errors. Some 80% of the technical failures are femoral tunnel malposition and 37% are tibial tunnel malposition.

SUMMARY

Ligament repair. One example is a method of calibrating an endoscopic optical system, the method comprising: placing an endoscope in a calibration assembly, the calibration assembly holds the endoscope in a fixed relationship to a calibration target on an inside surface of the calibration assembly; capturing, by a surgical controller, a plurality of images of the calibration target, each image captured at a unique rotational relationship between a camera head and the endoscope, the unique rotational relationships relative to a longitudinal central axis of the endoscope; and creating, by the surgical controller, a characterization function that characterizes optical distortion between the calibration target and a capture array of the camera head.

In the example method of calibrating the endoscope, placing the endoscope in the calibration assembly may further comprise placing the endoscope in the calibration assembly such that a viewing direction of a distal end of the endoscope is perpendicular to the calibration target. In the example method of calibrating the endoscope, placing the endoscope in the calibration assembly may further comprise placing the endoscope in the calibration assembly such that a viewing direction of a distal end of the endoscope is not perpendicular to the calibration target. In the example method of calibrating the endoscope, placing the endoscope in the calibration assembly may further comprises placing the endoscope in the calibration assembly such that a longitudinal central axis of the endoscope intersects a center of the calibration target and a viewing angle of a distal end of the endoscope is perpendicular to the calibration target.

The example method of calibrating the endoscope may further comprise placing water within an internal volume of the calibration assembly such that the internal volume between the calibration target and a distal end of the endoscope is filled with water or saline.

In the example method of calibrating the endoscope, capturing the plurality of images may further comprise: capturing a first image of the calibration target at a first rotational orientation between the endoscope and the camera head; and then capturing a second image of the calibration target at a second rotational orientation between the endoscope and the camera head; and then capturing a third image of the calibration target at a third rotational orientation between the endoscope and the camera head.

In the example method of calibrating the endoscope, capturing the plurality of images may further comprises capturing the plurality of images of the calibration target with a fixed relationship between the endoscope and the calibration assembly.

In the example method of calibrating the endoscope, creating the characterization may function further comprise creating the characterization function that includes calibration for determining orientation of fiducial markers by way of the endoscope having a single optical path through the endoscope.

Yet another example is a calibration assembly for calibrating an endoscopic optical system, the calibration assembly comprising: a vessel defining an internal volume, and the internal volume defining a calibration surface; a calibration target disposed on the calibration surface; a wall of the vessel defining an aperture into the vessel, the aperture defines a central axis that intersects the calibration target; an axial retention surface defined by the wall associated with the aperture, the axial retention surface a predetermined distance from the calibration target measured along the central axis of the aperture; and a rotational retention surface associated with the wall.

In the example calibration assembly, the rotational retention surface may further comprise a ridge disposed within a counterbore defined by the wall, and the rotational retention surface defined by opposing walls of the ridge. The ridge may be parallel to the central axis of the aperture.

In the example calibration assembly, the wall may further comprise a notch defining a channel with a closed bottom forming the axial retention surface, two sides forming the rotational retention surface, and an open top. The channel of the notch may be perpendicular to the central axis of the aperture.

In the example calibration assembly, the rotational retention surface may further comprises a clip configured to hold light post of an endoscope.

In the example calibration assembly, the calibration surface may be planar. In the example calibration assembly, the calibration surface may define a first portion that defines a first plane, and a second portion that defines a second plane, and wherein the first plane and the second plane are non-planar.

In the example calibration assembly, the wall of the vessel associated with the aperture may further comprise a tube defining an internal passageway, the tube protrudes from the vessel, and the internal passageway defining the aperture through the wall of the vessel.

In the example calibration assembly, the central axis of the aperture may intersect a center of the calibration target. In the example calibration assembly, the central axis of the aperture may form an acute angle with a vector normal to the calibration surface, the acute angle is non-zero.

Yet another example is a system for calibrating an endoscopic optical system, the system comprising: an endoscopic system comprising an endoscope and a camera head coupled to the endoscope, the endoscope defines a longitudinal central axis and a light post; and a calibration assembly. The calibration assembly may comprise: a vessel defining an internal volume; a calibration surface defined on an inside surface of the vessel; a calibration target disposed on the calibration surface; and an aperture defined through a wall of the vessel, and the endoscope telescoped through the aperture such that the longitudinal central axis intersects the calibration target. The calibration assembly may be configured to hold a distal end of the endoscope a predetermined distance from the calibration target, the calibration assembly may be configured to hold the endoscope in a fixed rotational orientation relative to the calibration target.

In the example system for calibrating the endoscopic optical system, the calibration assembly may further comprises a set of rotational retention surfaces defined by a ridge disposed within a counterbore defined by the wall, the set of rotational retention surfaces defined by opposing walls of the ridge, and wherein the set of rotational retention surfaces hold the endoscope in the fixed rotational orientation relative to the calibration target.

In the example system for calibrating the endoscopic optical system, the calibration assembly may further comprise a notch defining a channel with a closed bottom and an open top, the light post disposed within the notch, and wherein the notch holds the distal end of the of the endoscope the predetermined distance from the calibration target, and the notch holds the endoscope in the fixed rotational orientation relative to the calibration target.

In the example system for calibrating the endoscopic optical system, the calibration assembly may further comprise a clip coupled to the light post, the clip holds the endoscope in the fixed rotational orientation relative to the calibration target.

The example system for calibrating the endoscopic optical system may further comprise water within the internal volume between the distal end of the endoscope and the calibration target. The water may be saline.

In the example system for calibrating the endoscopic optical system, the calibration surface may be planar. In the example system for calibrating the endoscopic optical system, the calibration surface may defines a first portion that defines a first plane, and a second portion that defines a second plane, and wherein the first plane and the second plane are non-planar.

In the example system for calibrating the endoscopic optical system, the calibration assembly may further comprise a tube defining an internal passageway, and the tube protrudes from the vessel, the endoscope telescoped through the internal passageway such that the distal end of the endoscope resides within the internal volume of the vessel.

In the example system for calibrating the endoscopic optical system, the longitudinal central axis of the endoscope may intersects a center of the calibration target. In the example system for calibrating the endoscopic optical system, the longitudinal central axis of the endoscope may form an acute angle with a vector normal to the calibration surface, the acute angle is non-zero.

Yet still another example is an intraoperative method comprising: receiving, by a surgical controller, a three-dimensional bone model of a bone; receiving, by the surgical controller, images of a bone as viewed by an endoscope and attached camera head during a surgical procedure, the images of the bone including images of a fiducial coupled to the bone; receiving, by the surgical controller, a plurality of locations of an outer surface of the bone shown in the images of the bone; registering, by the surgical controller, the three-dimensional bone model to the bone using the plurality of locations; displaying, by the surgical controller on a display device, a representation of the three-dimensional bone model overlaid on images of the bone; and receiving, by the surgical controller, an indication that the three-dimensional bone model is correctly registered to the bone in the images of the bone.

In the example intraoperative method, receiving images of bone may further comprise receiving at least one selected from a group consisting of: images of an intercondylar notch of a femur; and images of an intercondylar ridge of a tibia. In the example intraoperative method, receiving the three-dimensional bone model may further comprise receiving the three-dimensional bone model constructed by segmentation of preoperative images of the bone.

In the example intraoperative method, receiving the plurality of locations of the outer surface of the bone may further comprise tracking, by the surgical controller, location of a distal tip of a touch probe as the touch probe abuts the bone in a plurality of locations. Tracking location of the distal tip of the touch probe may further comprise at least one selected from a group consisting of: tracking a fiducial disposed on an outer surface of the touch probe, the fiducial visible in the images of the bone as viewed by the endoscope and attached camera head; and tracking a fiducial array coupled to the touch probe as seen by a stereoscopic camera.

In the example intraoperative method, displaying the representation of the three-dimensional bone model may further comprise overlaying a mesh model representative of the three-dimensional bone model on the images of the bone shown on the display device.

Another example is a surgical controller comprising: a processor configured to couple to a display device; and a memory coupled to the processor. The memory stores instructions that, when executed by the processor, cause the processor to: receive a three-dimensional bone model of a bone; receive images of a bone as viewed by an endoscope and attached camera head during a surgical procedure, the images of the bone including images of a fiducial coupled to the bone; receive a plurality of locations of an outer surface of the bone shown in the images of the bone; register the three-dimensional bone model to the bone using the plurality of locations; display a representation of the three-dimensional bone model overlaid on images of the bone; and receive an indication that the three-dimensional bone model is correctly registered to the bone in the images of the bone.

In the example surgical controller, when the surgical controller receives images of the bone, the instructions may further cause the processor to receive at least one selected from a group consisting of: images of an intercondylar notch of a femur; and images of an intercondylar ridge of a tibia. In the example surgical controller, when the surgical controller receives the three-dimensional bone model, the instructions may further cause the processor to receive the three-dimensional bone model constructed by segmentation of preoperative images of the bone. In the example surgical controller, when the surgical controller receives the plurality of locations of the outer surface of the bone, the instructions may further cause the processor to track location of a distal tip of a touch probe as the touch prove abuts the bone in a plurality of locations. In the example surgical controller, when the surgical controller tracks location of the distal tip of the touch probe, the instructions may further cause the processor to at least one selected from a group consisting of: track a fiducial disposed on an outer surface of the touch probe, the fiducial as seen in the images of the bone as viewed by the endoscope and attached camera head; and track a fiducial array coupled to the touch probe as seen by a stereoscopic camera.

In the example surgical controller, when the surgical controller displays the representation of the three-dimensional bone model, the instructions may further cause the processor to overlay a mesh model representative of the three-dimensional bone model on the images of the bone.

Yet another example is an intraoperative method comprising: displaying, by a surgical controller on a display device, a planned-tunnel path for a ligament repair, the planned-tunnel path shown with respect to at least a portion of a bone, and the planned-tunnel path selected preoperatively; receiving, by the surgical controller during a surgical procedure, a revised-tunnel entry location; calculating, by the surgical controller during the surgical procedure, a revised-tunnel path through the bone, and displaying the revised-tunnel path on the display device; tracking, by the surgical controller and prior to drilling, an axial alignment of a drill axis of a drill wire relative to a longitudinal central axis of the revised-tunnel path; and displaying, by the surgical controller, a graphic on the display device that shows relative locations of the drill axis and the longitudinal central axis of the revised-tunnel path.

In the intraoperative method, the planned-tunnel path may be for an anterior cruciate ligament (ACL) repair.

In the intraoperative method, after calculating the revised-tunnel path, the method may further comprise: determining, by the surgical controller, a value indicative of overlap of the planned-tunnel path and the revised-tunnel path; and displaying, by the surgical controller on the display device, a visual representation of the value indicative of overlap of the planned-tunnel path and the revised tunnel path.

The intraoperative method may further comprise: calculating, by the surgical controller, an entry-location offset between a planned-tunnel entry of the planned-tunnel path and the revised-tunnel entry of the revised-tunnel path; calculating, by the surgical controller, an exit-location offset between a planned-tunnel exit of the planned-tunnel path and the revised-tunnel exit of the revised-tunnel path; and displaying, by the surgical controller on the display device, a visual representation of the entry-location offset and the exit-location offset.

The intraoperative method may further comprise: ascertaining, by the surgical controller, a value indicative of potential for posterior wall blowout of the revised-tunnel path; and displaying, by the surgical controller on the display device, a visual representation of the value indicative of potential for back wall blowout. In the intraoperative method, ascertaining the value indicative of potential for back wall blowout may further comprise measuring a distance between the revised-tunnel path and an outside surface of a three-dimensional bone model. Measuring the distance between the revised-tunnel path and the outside surface of the three-dimensional bone model may further comprises measuring a shortest distance between the revised-tunnel path and the outside surface of the three-dimensional bone model.

In the intraoperative method, displaying the planned-tunnel path may further comprise displaying at least one selected from a group consisting of: the planned-tunnel path through a femur; and the planned-tunnel path through a tibia.

In the intraoperative method, receiving the revised-tunnel entry location may further comprises receiving, by the surgical controller, the revised-tunnel entry location disposed within at least one selected from a group consisting of: an intercondylar notch of a femur; and an intercondylar ridge of a tibia.

In the intraoperative method, receiving the revised-tunnel entry location may further comprise receiving based on location of a distal tip of an aimer visible within the surgical cite by way of an endoscope and attached camera head.

In the intraoperative method, tracking the axial alignment may further comprise tracking axial alignment of an aimer through which the drill wire telescopes.

In the intraoperative method, tracking axial alignment of the aimer may further comprises: receiving, by the surgical controller, images by way of an endoscope and attached camera head, the images comprising a fiducial disposed on an outside surface of the aimer; and calculating, by the surgical controller based on the images, axial alignment of the aimer relative to a three-dimensional model of an exterior surface of the bone.

The intraoperative method may further comprise: tracking, by the surgical controller, the drill axis of the drill wire during drilling, the drilling creates a throughbore with a central axis; and displaying, by the surgical controller on the display device, a value indicative of offset between the central axis of the throughbore and the longitudinal central axis of the revised-tunnel path.

In the intraoperative method, displaying the graphic that shows relative locations of the drill axis and the longitudinal central axis of the revised-tunnel path may further comprise: displaying a tunnel-path target indicative of the longitudinal central axis of the revised-tunnel path; displaying a distal-end target indicative of location of the distal end of the drill wire relative to the longitudinal central axis of the revised-tunnel path; and displaying a proximal-end target indicative of location of a more-proximal end of the axial alignment of the drill wire relative to the longitudinal central axis of the revised-tunnel path.

Yet another example is a surgical controller comprising: a processor configured to couple to a display device; and a memory coupled to the processor. The memory stores instructions that, when executed by the processor, cause the processor to: receive images of a leg bone as viewed by an endoscope and attached camera head during a surgical procedure; display on the display device a planned-tunnel path for an anterior cruciate ligament (ACL) repair, the planned-tunnel path shown with respect to at least a portion of the leg bone; receive a revised-tunnel entry location; calculate a revised-tunnel path through the leg bone, the revised-tunnel path having a longitudinal central axis; display the revised-tunnel path on the display device; track an axial alignment of a drill axis of a drill wire relative to the longitudinal central axis; and display a graphic on the display device that shows relative locations of the drill axis and the longitudinal central axis of the revised-tunnel path.

In the example surgical controller, after the processor calculates the revised-tunnel path, the instructions may further cause the processor to: determine a value indicative of overlap of the planned-tunnel path and the revised-tunnel path; and display on the display device a visual representation of the value indicative of overlap of the planned-tunnel path and the revised-tunnel path.

In the example surgical controller, the instructions may further cause the processor to: calculate an entry-location offset between a planned-tunnel entry of the planned-tunnel path and the revised-tunnel entry of the revised-tunnel path; calculate an exit-location offset between a planned-tunnel exit of the planned-tunnel path and the revised-tunnel exit of the revised-tunnel path; and display on the display device a visual representation of the entry-location offset and the exit-location offset.

In the example surgical controller, the instructions may further cause the processor to: ascertain a value indicative of potential for back wall blowout of the revised-tunnel path; and display on the display device a visual representation of the value indicative of potential for back wall blowout. In the example surgical controller, when the processor ascertains the value indicative of potential for back wall blowout, the instructions may further cause the processor to measure a distance between the revised-tunnel path and an outside surface of a three-dimensional bone model. In the example surgical controller, when the processor measures the distance between the revised-tunnel path and the outside surface of the three-dimensional bone model, the instructions may further cause the processor to measure a shortest distance between the revised-tunnel path and the outside surface of the three-dimensional bone model.

In the example surgical controller, when the processor displays the revised-tunnel path, the instructions may further cause the processor to display at least one selected from a group consisting of: the planned-tunnel path through a femur; and the planned-tunnel path of through a tibia.

In the example surgical controller, when the processor receives the revised-tunnel entry location, the instructions cause the processor to receive the revised-tunnel entry location disposed within at least one selected from a group consisting of: an intercondylar notch of a femur; and an intercondylar ridge of a tibia.

In the example surgical controller, when the processor receives the revised-tunnel entry location, the instructions may further cause the processor to receive based on location of a distal tip of an aimer visible within the images of a bone as viewed by the endoscope and attached camera head.

In the example surgical controller, when the processor tracks the axial alignment, the instructions may further cause the processor to track the axial alignment of an aimer through which the drill wire telescopes, the aimer visible within the images of a bone as viewed by the endoscope and attached camera head. In the example surgical controller, when the processor receives images of the bone as viewed by the endoscope and attached camera head, the instructions may further cause the processor to receive images comprising a fiducial disposed on an outside surface of the aimer; and when the processor tracks the axial alignment of the aimer, the instructions may further cause the processor to calculate, based on orientation of the fiducial, the axial alignment of the aimer relative to a three-dimensional model of an exterior surface of the bone.

In the example surgical controller, the instructions may further cause the processor to: track the drill axis of the drill wire during drilling, the drilling creates a throughbore with a central axis; and display on the display device a value indicative of offset between the central axis of the throughbore and the longitudinal central axis of the revised-tunnel path.

In the example surgical controller, when the processor displays the graphic that shows relative locations of the drill axis and the longitudinal central axis of the revised-tunnel path, the instructions may further cause the processor to: display a tunnel-path target indicative of the longitudinal central axis of the revised-tunnel path; display a distal-end target indicative of location of the distal end of the drill wire relative to the longitudinal central axis of the revised-tunnel path; and display a proximal-end target indicative of location of a more-proximal end of the axial alignment of the drill wire relative to the longitudinal central axis of the revised-tunnel path.

BRIEF DESCRIPTION OF THE DRAWINGS

For a detailed description of example embodiments, reference will now be made to the accompanying drawings in which.

DEFINITIONS

Figure 2:
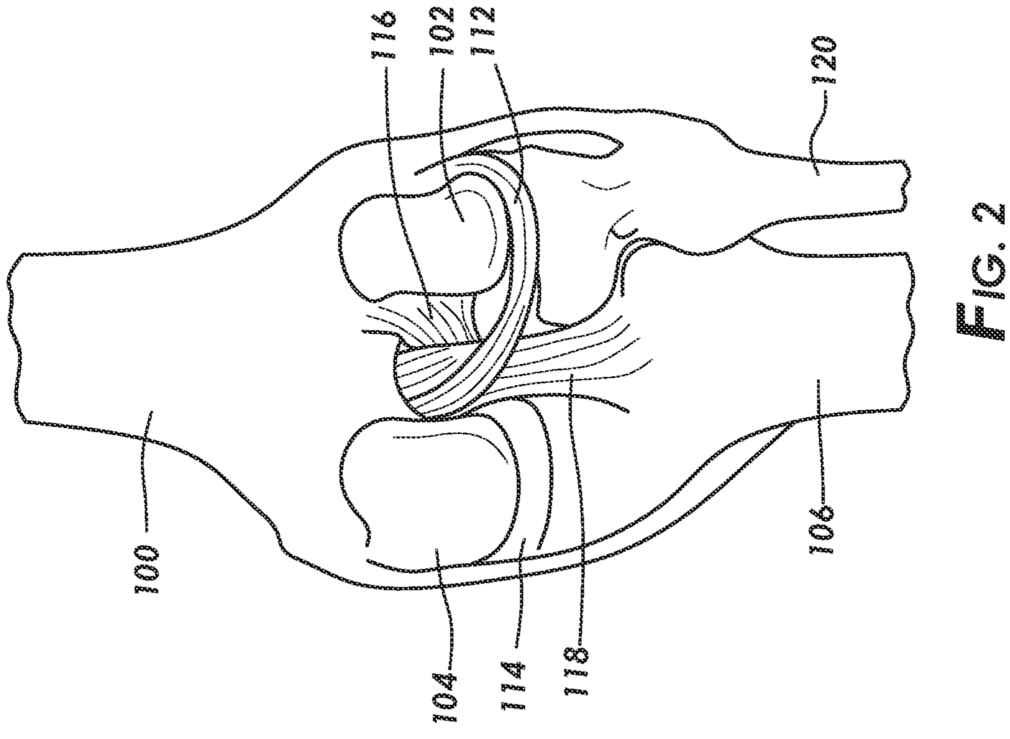
FIG. 2 shows a posterior or back elevation view of the right knee.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

"Receiving . . . a . . . location" shall mean receiving data indicative of location on a bone within a coordinate space (e.g., a coordinate space of a view of an endoscope). Thus, example systems and methods may "receive . . . a revised-tunnel entry location" being data indicative of a proposed location of a tunnel entry point within a three-dimensional coordinate space. Other example systems and methods may "receive . . . a plurality of locations on a bone" being data indicative locations of an outer surface of a bone as part of registering a bone to a three-dimensional bone model.

An endoscope having "a single optical path" through an endoscope shall mean that the endoscope is not a stereoscopic endoscope having two distinct optical paths separated by an interocular distance at the light collecting end of the endoscope. The fact that an endoscope has two or more optical members (e.g., glass rods, optical fibers) forming a single optical path shall not obviate the status as a single optical path.

"Throughbore" shall mean an aperture or passageway through an underlying device. However, the term "throughbore" shall not be read to imply any method of creation. Thus, a throughbore may be created in any suitable way, such as drilling, boring, laser drilling, or casting.

"Counterbore" shall mean an aperture or passageway into an underlying device. In cases in which the counterbore intersects another aperture (e.g., a throughbore), the counterbore may thus define an internal shoulder. However, the term "counterbore" shall not be read to imply any method of creation. A counterbore may be created in any suitable way, such as drilling, boring, laser drilling, or casting.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to methods and systems of ligament reconstruction and repair. The ligament repair (e.g., anterior cruciate ligament (ACL) repair) may be performed arthroscopically and computer assisted. Some examples include methods and systems of calibrating an endoscopic optical system comprising an arthroscope and attached camera head. The calibration is to account for optical distortion present within the optical pathways such that the images created by the arthroscope and attached camera head may be used in the arthroscopic repair, such as for registering a bone model to the bone visible through the arthroscope, tracking location of various objects within the surgical site with respect bone model, and/or intraoperatively updating tunnel locations. Other examples include verification of registration of a three-dimensional bone model to the bone visible through the arthroscope. Yet still other examples include making intraoperative changes to the tunnel paths for the ligament repair, and then creating the tunnels along the revised-tunnel paths.

The various examples were developed in the context of ACL repair, and thus the discussion below is based on the developmental context. However, the techniques are applicable to many types of ligament repair, such as medial collateral ligament repair, lateral collateral ligament repair, and posterior cruciate ligament repair. Moreover, the various example methods and systems can also be used for planning and placing anchors to reattach soft tissue, such as reattaching the labrum of the hip, the shoulder, or the meniscal root. Thus, the description and developmental context shall not be read as a limitation of the applicability of the teachings. In order to orient the reader, the specification first turns a description of the knee.

Figure 1:
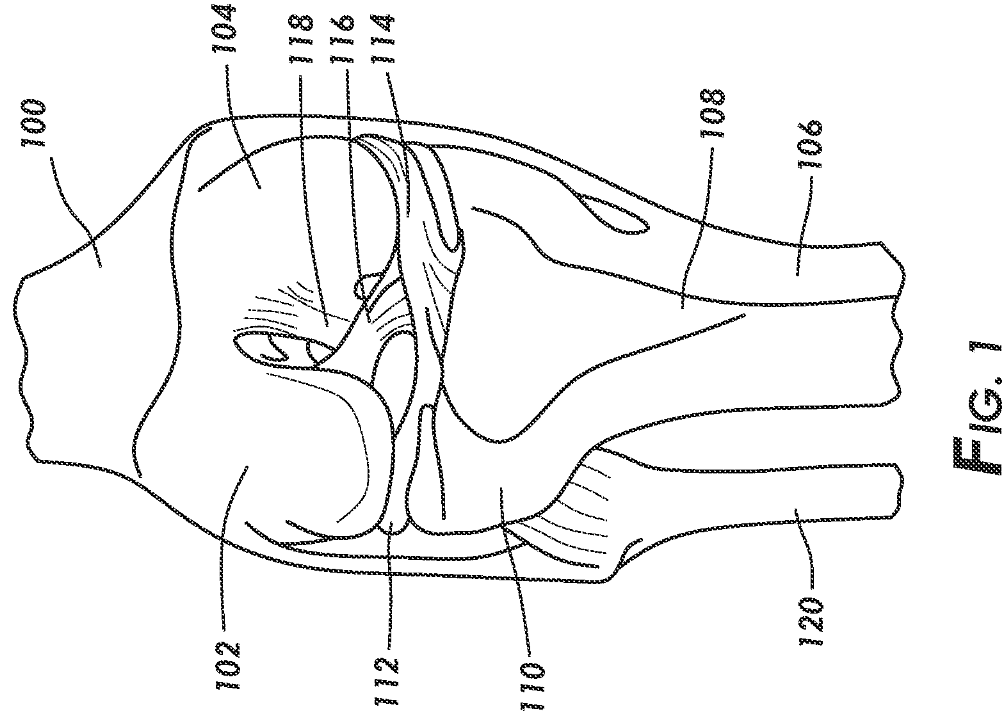
FIG. 1 shows an anterior or front elevation view of right knee, with the patella removed.

FIG. 1 shows an anterior or front elevation view of a right knee, with the patella removed. In particular, visible in FIG. 1 is lower portion of the femur 100 including the outer or lateral condyle 102 and the inner or medial condyle 104. The femur 100 and condyles 102 and 104 are in operational relationship to a tibia 106 including the tibial tuberosity 108 and Gerdy's tubercle 110. Disposed between the femoral condyles 102 and 104 and the tibia 106 are the lateral meniscus 112 and the medial meniscus 114. Several ligaments are also visible in the view of FIG. 1, such as the ACL 116 extending from the lateral side of femoral notch to the medial side of the tibia 106. Oppositely, the posterior cruciate ligament 118 extends from medial side of the femoral notch to the tibia 106. Also visible is the fibula 120, and several additional ligaments that are not specifically numbered.

FIG. 2 shows a posterior or back elevation view of the right knee. In particular, visible in FIG. 2 is lower portion of the femur 100 including the lateral condyle 102 and the medial condyle 104. The femur 100 and femoral condyles 102 and 104 again are in operational relationship to the tibia 106, and disposed between the femoral condyles 102 and 104 and the tibia 106 are the lateral meniscus 112 and the medial meniscus 114. FIG. 2 further shows the ACL 116 extending from the lateral side of femoral notch to the medial side of the tibia 106, though the attachment point to the tibia 106 is not visible. The posterior cruciate ligament 118 extends from medial side of the femoral notch to the tibia 106, though the attachment point to the femur 100 not visible. Again, several additional ligaments are shown that are not specifically numbered.

The most frequent ACL injury is a complete tear of the ligament. Treatment involves reconstruction of the ACL by placement of a substitute graft (e.g., autograft from either the patellar tendon, quad tendon, or the hamstring tendons). The graft is placed into tunnels prepared within the femur 100 and the tibia 106. The current standard of care for ACL repair is to locate the tunnels such that the tunnel entry point for the graft is at the anatomical attachment location of the native ACL. Such tunnel placement at the attachment location of the native ACL attempts to recreate original knee kinematics. In arthroscopic surgery, the location of the tunnel through the tibia 106 is relatively easy to reach, particularly when the knee is bent or in flexion. However, the tunnel through the femur 100 resides within the intercondylar notch. Depending upon the physical size of the patient and the surgeon's selection for location of the port through the skin, and through which the various instruments are inserted into the knee, it may be difficult to reach the attachment location of the native ACL to the femur 100.

Figure 3:
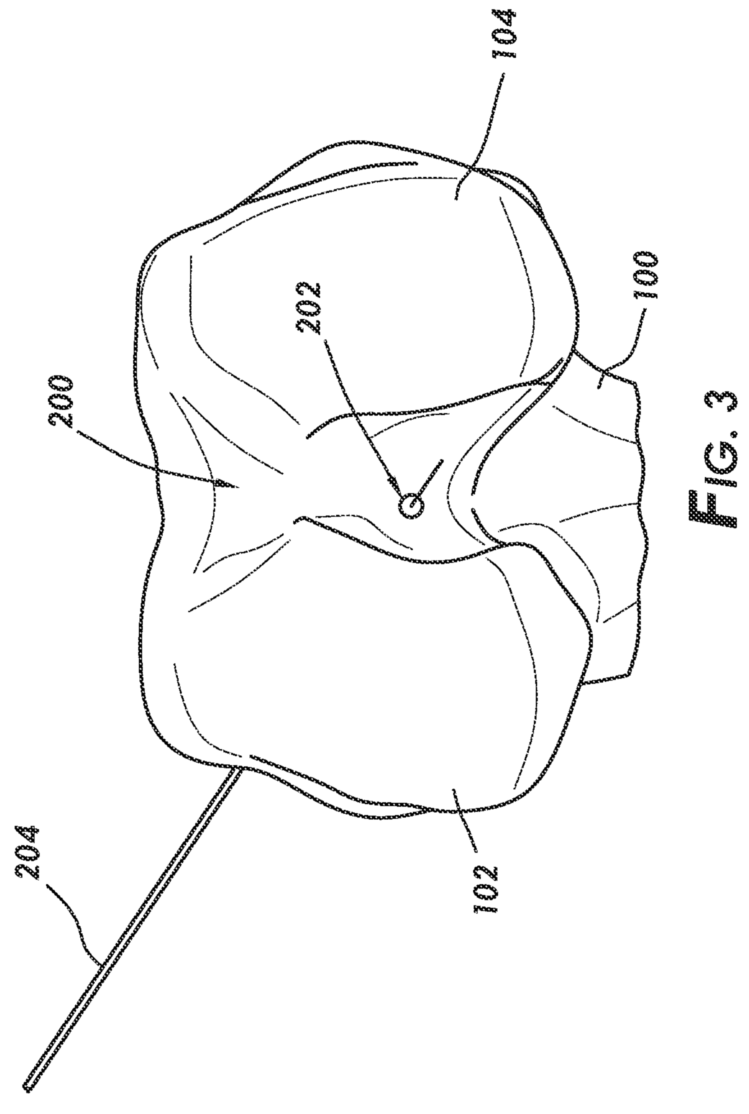
FIG. 3 shows a view of the femur from below and looking into the intercondylar notch.

FIG. 3 shows a view of the femur from below and looking into the intercondylar notch. In particular, visible in FIG. 3 are the lateral condyle 102 and the medial condyle 104. Defined between the femoral condyles 102 and 104 is the femoral notch 200. The femoral tunnel may define inside aperture 202 within the femoral notch 200, the inside aperture 202 closer to the lateral condyle 102 and displaced into the posterior portion of the femoral notch 200. The femoral tunnel extends through the femur 100 and forms an outside aperture on the outside or lateral surface of the femur 100 (the outside aperture not visible in FIG. 3). FIG. 3 shows an example drill wire 204 that may be used to create an initial tunnel or pilot hole. Once the surgeon verifies that the pilot hole is closely aligned with a planned-tunnel path, the femoral tunnel is created by boring or reaming with another instrument (e.g., a reamer) that may use the drill wire 204 as a guide. In some cases, a socket or counter-bore is created on the intercondylar notch side to accommodate the width of the graft that extends into the bone, and that counterbore may also be created using another instrument (e.g., reamer) that may use the drill wire 204 as a guide.

Drilling of a tunnel may take place from either direction. Considering the femoral tunnel again as an example, the tunnel may be drilled from the outside or lateral portion of the femur 100 toward and into the femoral notch 200, which is referred to as an "outside-in" procedure. Oppositely, the example femoral tunnel may be drilled from the inside of the femoral notch 200 toward and to the lateral portion of the femur 100, which is referred as an "inside-out" procedure. The various examples discussed below are equally applicable to outside-in or inside-out procedures. Outside-in procedures may additionally use a device which holds the drill wire on the outside portion, and physically shows the expected tunnel location of the inside aperture within the knee. However, the device for the outside-in procedure is difficult to use in arthroscopic procedures, and thus many arthroscopic repairs use the inside-out procedure. The further examples discussed below are thus based on an inside-out procedure, but such should not be read as a limitation. The specification now turns to an example surgical system.

Figure 4:
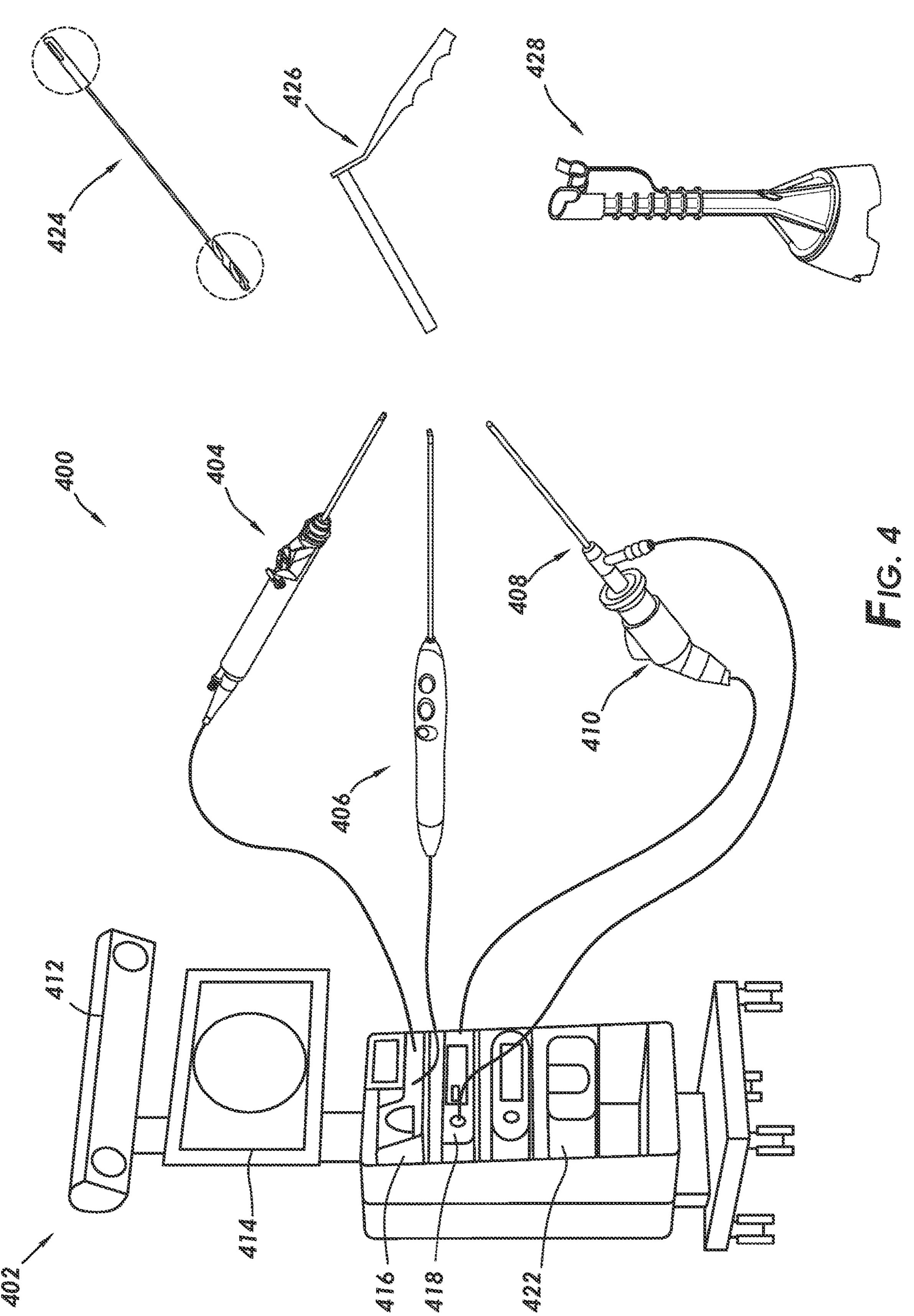
FIG. 4 shows a surgical system in accordance with at least some embodiments.

FIG. 4 shows a surgical system (not to scale) in accordance with at least some embodiments. In particular, the example surgical system 400 comprises a tower or device cart 402, an example mechanical resection instrument 404, an example plasma-based ablation instrument (hereafter just ablation instrument 406), and an endoscope in the example form of an arthroscope 408 and attached camera head 410. The endoscope 408 defines a light connection or light post 420 to which light is provided, and the light is routed internally within the endoscope 408 to illuminate a surgical field at the distal end of the endoscope 408. The device cart 402 may comprise a camera 412 (illustratively shown as a stereoscopic camera), a display device 414, a resection controller 416, and a camera control unit (CCU) together with an endoscopic light source and video controller 418. In example cases the CCU and video controller 418 provides light to the light post 420 of the arthroscope 408, displays images received from the camera head 410. In example cases, the CCU and video controller 418 also implements various additional aspects, such as calibration of the arthroscope and camera head, displaying planned-tunnel paths on the display device 414, receiving revised-tunnel entry locations, calculating revised-tunnel paths, and calculating and displaying various parameters that show the relationship between the revised-tunnel path and the planned-tunnel path. Thus, the CCU and video controller is hereafter referred to as surgical controller 418. In other cases, however, the CCU and video controller may be a separate and distinct system from the controller that handles aspects of intraoperative changes, yet the separate devices would nevertheless be operationally coupled.

The example device cart 402 further includes a pump controller 422 (e.g., single or dual peristaltic pump). Fluidic connections of the mechanical resection instrument 404 and ablation instrument 406 are not shown so as not to unduly complicate the figure. Similarly, fluidic connections between the pump controller 422 and the patient are not shown so as not to unduly complicate the figure. In the example system, both the mechanical resection instrument 404 and the ablation instrument 406 are coupled to the resection controller 416 being a dual-function controller. In other cases, however, there may be a mechanical resection controller separate and distinct from an ablation controller. The example devices and controllers associated with the device cart 402 are merely examples, and other examples include vacuum pumps, patient-positioning systems, robotic arms holding various instruments, ultrasonic cutting devices and related controllers, patient-positioning controllers, and robotic surgical systems.

FIG. 4 further shows additional instruments that may be present during an example ACL repair. In particular, FIG. 4 shows an example guide wire or drill wire 424 and an aimer 426. The drill wire 424 may be used to create an initial or pilot tunnel through the bone. In some cases, the diameter of the drill wire may be about 2.4 millimeters (mm), but larger and smaller diameters for the drill wire 424 may be used.

The example drill wire 424 is shown with magnified portions on each end, one to show the cutting elements on the distal end of the drill wire 242, and another magnified portion to show a connector for coupling to chuck of a drill. Once the surgeon drills the pilot tunnel, the surgeon and/or the surgical controller 418 (discussed more below) may then assess whether the pilot tunnel matches or closes matches the planned-tunnel path. If the pilot tunnel is deemed sufficient, then the drill wire 424 may be used as a guide for creating the full-diameter throughbore for the tunnel, and possibly also for creating a counterbore associated with intercondylar notch to accommodate the graft. While in some cases the drill wire alone may be used when creating the pilot tunnel, in yet still other cases the surgeon may use the aimer 426 to help guide and place the drill wire 424 at the designed tunnel-entry location.

FIG. 4 also shows that the example system may comprise a calibration assembly 428. As will be discussed in greater detail below, the calibration assembly 428 may be used to detect optical distortion in images received by the surgical controller 418 through the arthroscope 408 and attached camera head 410. Additional tools and instruments will be present, such as a drill for drilling with the drill wire 424, various reamers for creating the throughbore and counterbore aspects of the tunnel, and various tools for suturing and anchoring the graft in place. These additional tools and instruments are not shown so as not to further complicate the figure.

The specification now turns to a workflow for an example ACL repair. The workflow may be conceptually divided into a preoperative planning and intraoperative repair. The intraoperative repair workflow may be further conceptually divided into optical system calibration, model registration, intraoperative tunnel-path planning, intraoperative tunnel creation, and intraoperative tunnel placement analysis. Each will be addressed in turn.

Planning

In accordance with various examples, an ACL repair starts with imaging (e.g., X-ray imaging, computed tomography (CT), magnetic resonance imaging (MRI)) of the knee of the patient, including the relevant anatomy like the lower portion of the femur, the upper portion of the tibia, and the articular cartilage. The discussion that follows assumes MRI imaging, but again many different types of imaging may be used. The MRI imaging can be segmented from the image slices such that a volumetric model or three-dimensional model of the anatomy is created. Any suitable currently available, or after developed, segmentation technology may be used to create the three-dimensional model. More specifically to the example of ACL repair and specifically selecting a tunnel path through the femur, a three-dimensional bone model of the lower portion of the femur, including the femoral condyles, is created.

Using the three-dimensional bone model, an operative plan is created that comprises choosing a planned-tunnel path through the femur, including locations of the apertures of the bone that define the ends of the tunnel. For an example inside-out repair, the aperture within the femoral notch is the entry location for the drilling, and the aperture on the lateral surface of the femur is the exit location. For an outside-in repair, the entry and exit locations for drilling are swapped. Still assuming an inside-out repair, the entry location may be selected to be the same as, or close to, the attachment location of the native ACL to the femur within the femoral notch. In some cases, selecting the entry location within the femoral notch may involve use of a Bernard & Hertel Quadrant or grid placed on a fluoroscopic image, or placing the Bernard & Hertel Quadrant on a simulated fluoroscopic image created from the three-dimensional bone model. Based on use of the Bernard & Hertel Quadrant, an entry location for the tunnel is selected. For an inside-out repair, selection of the exit location is less restrictive, not only because the portion of the tunnel proximate to the exit location is used for placement of the anchor for the graft, but also because the exit location is in approximately centered in the femur (considered anteriorly to posteriorly), and thus issues of bone wall thickness at the exit location are of less concern. In some cases, a three-dimensional bone model of the proximal end of the tibia is also created, and the surgeon may likewise choose planned-tunnel path(s) through the tibia.

The results of the planning may comprise: a three-dimensional bone model of the distal end of the femur; a three-dimensional bone model for a proximal end of the tibia; an entry location and exit location through the femur and thus a planned-tunnel path for the femur; and an entry location and exit location through the tibia and thus a planned-tunnel path through the tibia. Other surgical parameters may also be selected during the planning, such as tunnel throughbore diameters, tunnel counterbore diameters and depth, desired post-repair flexion, and the like, but those additional surgical parameters are omitted so as not to unduly complication the specification.

Intraoperative Repair

The specification now turns to intraoperative aspects. The intraoperative aspects include steps and procedures for setting up the surgical system to perform the various repairs. It is noted, however, that some of the intraoperative aspects (e.g., optical system calibration), may take place before any ports or incisions are made through the patient's skin, and in fact before the patient is wheeled into the surgical room. Nevertheless, such steps and procedures may be considered intraoperative as they take place in the surgical setting and with the surgical equipment and instruments used to perform the actual repair.

The example ACL repair is conducted arthroscopically and is computer-assisted in the sense the surgical controller 418 is used for arthroscopic navigation within the surgical site. More particularly, in example systems the surgical controller 418 provides computer-assistance during the ligament repair by tracking location of various objects within the surgical site, such as the location of the bone within the three-dimensional coordinate space of the view of the arthroscope, and location of the various instruments (e.g., the drill wire 424, the aimer 426) within the three-dimensional coordinate space of the view of the arthroscope. The specification turns to brief description of such tracking techniques.

Figure 5:
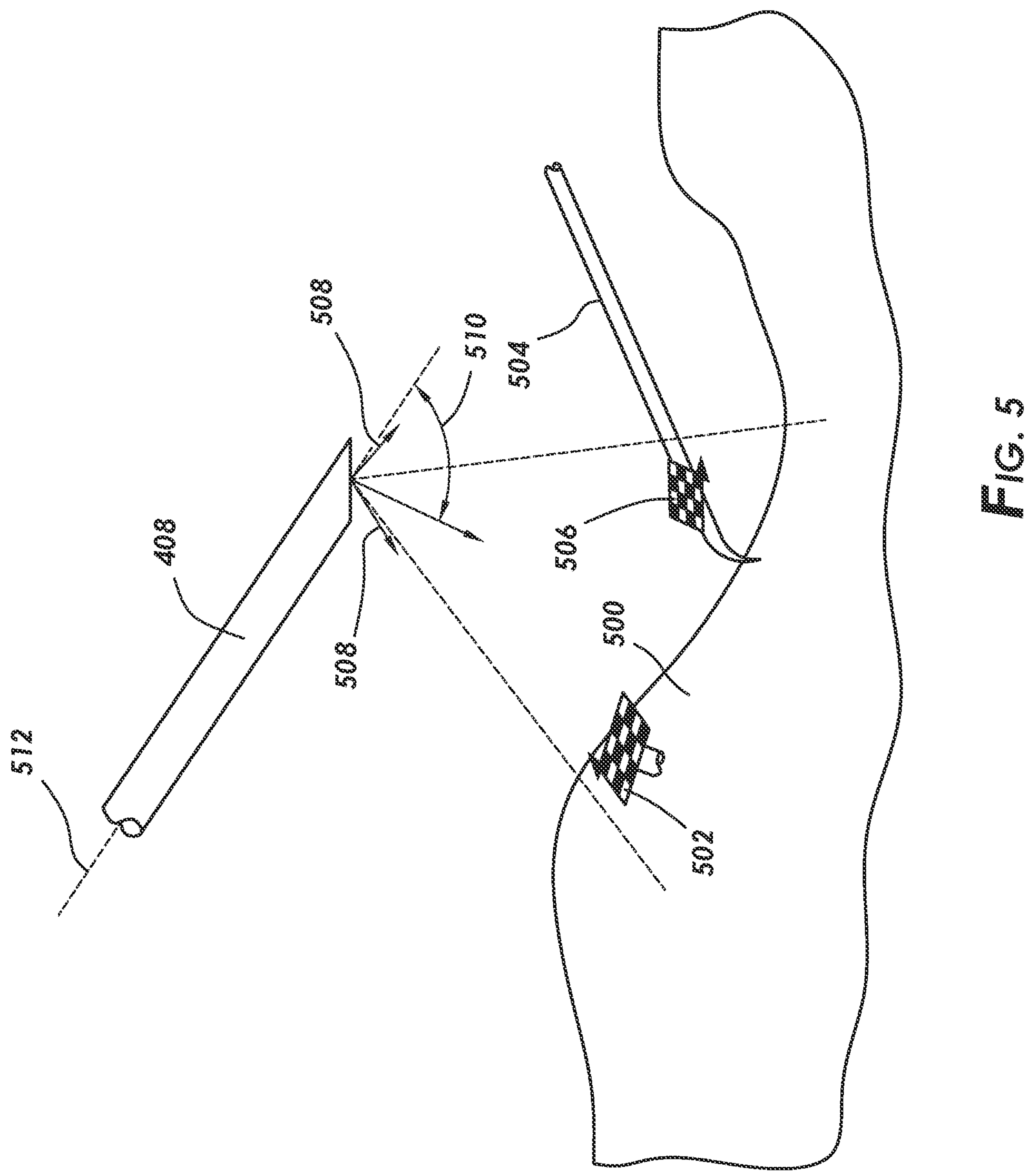
FIG. 5 shows a conceptual drawing of a surgical site with various objects within the surgical site tracked, in accordance with at least some embodiments.

FIG. 5 shows a conceptual drawing of a surgical site with various objects within the surgical site. In particular, visible in FIG. 5 is a distal end of the arthroscope 408, a portion of a bone 500 (e.g., femur), a bone fiducial 502 within the surgical site, a touch probe 504, and a probe fiducial 506. Each is addressed in turn.

The distal end of the arthroscope 408 is designed and constructed to illuminate the surgical site with visible light received by way of the light post 420 (FIG. 4). In the example of FIG. 5, the illumination is illustrated by arrows 508. The illumination provided to the surgical site is reflected by various objects and tissues within the surgical site, and the reflected light that returns to the distal end enters the arthroscope 408, propagates along an optical channel within the arthroscope 408, and is eventually incident upon a capture array within the camera head 410 (FIG. 4). The images detected by the capture array within the camera head 410 are sent electronically to the surgical controller 418 (FIG. 4) and displayed on the display device 414 (FIG. 4). In accordance with example systems, the arthroscope 408 has a single optical path through the arthroscope for capturing images of the surgical site, notwithstanding that the single optical path may be constructed of two or more optical members (e.g., glass rods, optical fibers). That is to say, in example systems and methods the computer-assisted navigation provided by the arthroscope 408, camera head 410, and surgical controller 418 is provided with the arthroscope 408 that is not a stereoscopic endoscope having two distinct optical paths separated by an interocular distance at the distal end endoscope.

During a surgical procedure, a surgeon selects an arthroscope with a viewing direction beneficial for the planned surgical procedure. Viewing direction refers to a line residing at the center of an angle subtended by the outside edges or peripheral edges of the view of an endoscope. The viewing direction for some arthroscopes is aligned with the longitudinal central axis of the arthroscope, and such arthroscopes are referred to as "zero degree" arthroscopes (e.g., the angle between the viewing direction and the longitudinal central axis of the arthroscope is zero degrees). The viewing direction of other arthroscopes forms a non-zero angle with the longitudinal central axis of the arthroscope. For example, for a 30° arthroscope the viewing direction forms a 30° angle to the longitudinal central axis of the arthroscope, the angle measured as an obtuse angle beyond the distal end of the arthroscope. In many cases for ACL repair, the surgeon selects a 30° arthroscope or a 45° arthroscope based on location the port created through the skin of the patient. In the example of FIG. 5, the view angle 510 of the arthroscope 408 forms a non-zero angle to the longitudinal central axis 512 of the arthroscope 408.

Still referring to FIG. 5, within the view of the arthroscope 408 is a portion of the bone 500, along with the bone fiducial 502, the touch probe 504, and the probe fiducial 506. The bone fiducial 502 is shown as a planar element having a pattern disposed thereon, though other shapes for the bone fiducial 502 may be used (e.g., a square block with a pattern on each face of the block). The bone fiducial 502 may be attached to the bone 500 in any suitable form (e.g., a fastener, such as a screw). The pattern of the bone fiducial is designed to provide information regarding the orientation of the bone fiducial 502 in the three-dimensional coordinate space of the view of the arthroscope 408. More particularly, the pattern is selected such that the orientation of the bone fiducial 502, and thus the orientation of the underlying bone 500, may be determined from images captured by the arthroscope 408 and attached camera head 410 (FIG. 4).

The probe fiducial 506 is shown as a planar element attached to the touch probe 504. The touch probe 504 may be used, as discussed more below, to "paint" the surface of the bone 500 as part of the registration of the bone 500 to the three-dimensional bone model, and the touch probe 504 may also be used to indicate revised-tunnel entry locations in the case of intraoperative changes to the tunnel paths. The probe fiducial 506 is shown as a planar element having a pattern disposed thereon, though other shapes for the probe fiducial 506 may be used (e.g., a square block surrounding the touch probe 504 with a pattern on each face of the block). The pattern of the probe fiducial 506 is designed to provide information regarding the orientation of the probe fiducial 506 in the three-dimensional coordinate space of the view of the arthroscope 408. More particularly, the pattern is selected such that the orientation of the probe fiducial 506, and thus the location of the point of the touch probe 504, may be determined from images captured by the arthroscope 408 and attached camera head 410 (FIG. 4).

Other instruments within the view of the arthroscope 408 may also have fiducials, such as the drill wire 424 (FIG. 4) and aimer 426 (FIG. 4), but the additional instruments are not shown so as not unduly complicate the figure. Moreover, in addition to or in place of tracking location based on the view through the arthroscope 408, the location of the distal end of one or more of the instruments may be tracked by other methods and systems. For example, for devices that rigidly extend out of the surgical site (e.g., the aimer 426 (FIG. 4)), the location may be tracked by an optical array coupled to the aimer and viewed through the camera 412 (FIG. 4), such as a stereoscopic camera. The location within the three-dimensional coordinate space of the camera 412 is then transformed into the three-dimensional coordinate space of the view of the example arthroscope to determine location of the distal end within the surgical site.

The images captured by the arthroscope 408 and attached camera head 410 are subject to optical distortion in many forms. For example, the visual field between distal end of the arthroscope 408 and the bone 500 within the surgical site is filled with fluid, such as bodily fluids and saline used to distend the joint. Many arthroscopes have one or more lenses at the distal end that widen the field of view, and creating wider field of view causes a "fish eye" effect in the captured images. Further, the optical elements within the arthroscope (e.g., rod lenses) may have optical aberrations inherent to the manufacturing and/or assembly process. Further still, the camera head 410 may have various optical elements for focusing the images receives onto the capture array, and the various optical elements may have aberrations inherent to the manufacturing and/or assembly process.

Optical System Calibration

In example systems, prior to use within each surgical procedure, the endoscopic optical system is calibrated to account for the various optical distortions. In particular, various embodiments comprise a system for calibrating the endoscopic optical system. Referring again to FIG. 4, the example system comprises the surgical controller 418, the arthroscope 408, the camera head 410, and the calibration assembly 428. In particular, the calibration may comprise placing the arthroscope 408 into the calibration assembly 428. The calibration assembly 428 holds the arthroscope 408 in a fixed relationship to a calibration target on an inside surface of the calibration assembly 428. Once the distal end of the arthroscope 408 is within the calibration assembly 428, the example method comprises capturing a plurality of images of the calibration target, with each image captured at a unique rotational relationship between the camera head 410 and the arthroscope 408, with the unique rotational relationships relative to a longitudinal central axis of the arthroscope 408. Using the plurality of images, the example surgical controller 418 creates a characterization function that characterizes optical distortion between the calibration target and the capture array within the camera head 410. The characterization function may include a calibration for determining orientation of fiducial markers visible within the surgical site (e.g., bone fiducial 502, probe fiducial 506) by way of the arthroscope 408 and attached camera head 410.

The specification now turns to a description of the example calibration assembly 428 in greater detail.

Figure 6:
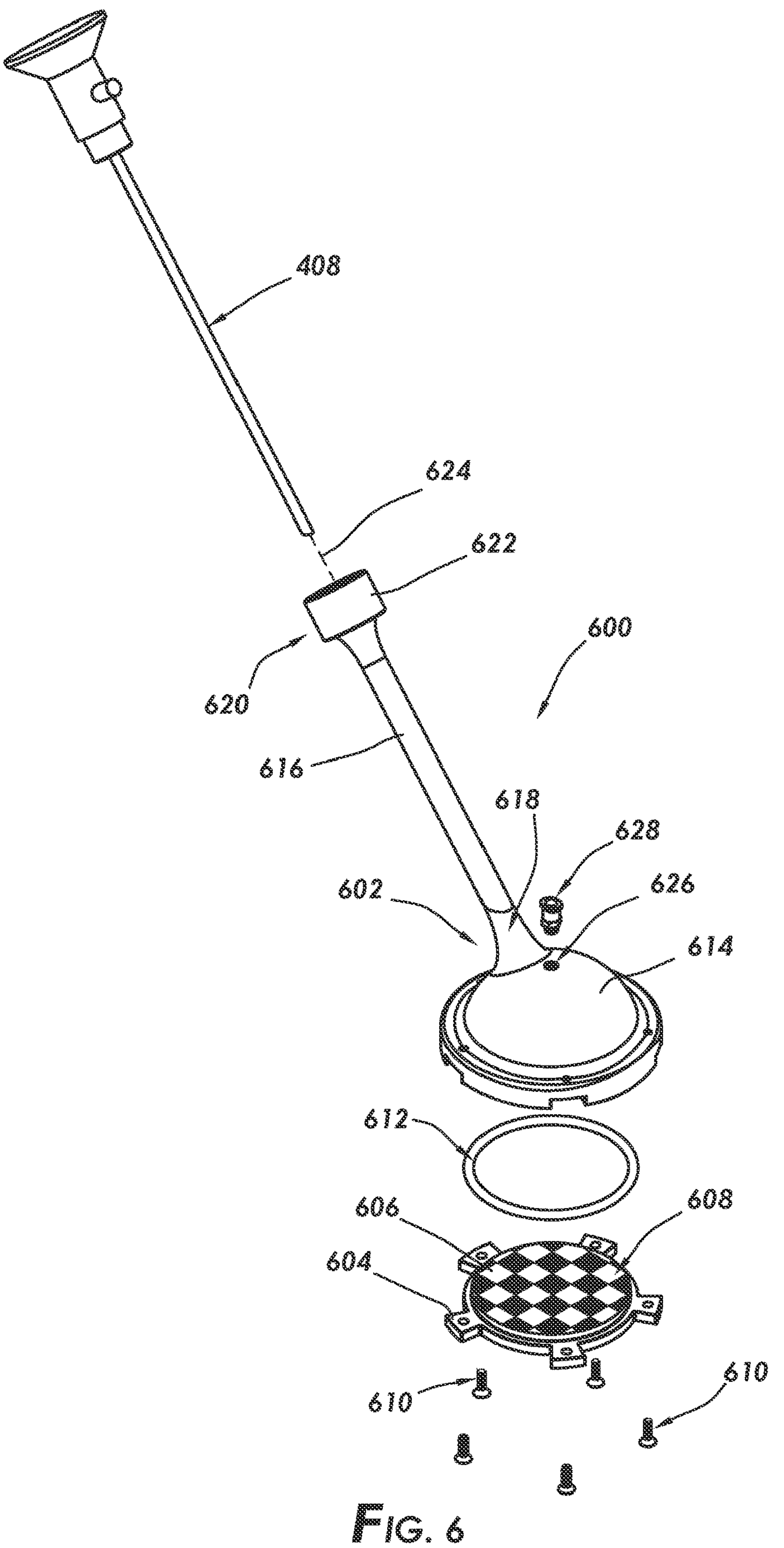
FIG. 6 shows an exploded perspective view of a calibration assembly, in accordance with at least some embodiments.

FIG. 6 shows an exploded perspective view of an example calibration assembly. In particular, FIG. 6 shows the arthroscope 408 (without the camera head) and the example calibration assembly 600. The calibration assembly 600 comprises an upper housing 602 and a lower housing 604. Working from the bottom of the calibration assembly 600 up, the lower housing 604 defines a calibration surface 606. When the lower housing 604 is coupled to the upper housing 602, the calibration surface 606 is thus disposed on an inside surface of an internal volume defined by the calibration assembly. Disposed on the calibration surface 606 is a calibration target 608. In the example of FIG. 6, the calibration target 608 is shown as a checkerboard pattern, but any suitable pattern with distinctive features may be used as the calibration target 608.

When assembled, the lower housing 604 couples to the upper housing 602, such as by fasteners 610. In use for calibration of an arthroscope 408, the internal volume of the calibration assembly 600 is filled with water, such as saline. In order to form a water tight seal, an example O-ring 612 is disposed between the upper housing 602 and the lower housing 604. In other cases, however, the O-ring may be omitted and the connection between the upper housing 602 and the lower housing 604 may be sealed in other ways (e.g., friction fit, friction weld). In yet still further cases, the upper housing 602 and lower housing 604 may be an integral component, and thus no fasteners or O-ring would be used.

The example upper housing 602 defines an enclosure or vessel 614 and a cylinder or tube 616. The vessel 614, along with lower housing 604, together define the internal volume within which the calibration surface 606 and calibration target 608 reside. The tube 616 has proximal end 618 coupled the vessel 614, and a distal end 620. As shown, the tube 616 protrudes from the vessel 614. The tube 616 defines a throughbore that extends from the distal end 620 to the proximal end 618. The throughbore is fluidly coupled to the internal volume of the vessel 614, and thus defines an aperture into the vessel 614. The throughbore further defines a longitudinal central axis 624. The distal end 620 of the tube defines a flange 622. The flange 622 defines features that perform several functions. First, the flange 622 defines features that, when the arthroscope 408 is telescoped into the tube 616 along the longitudinal central axis 624, hold the distal end of the arthroscope 408 at a predetermined distance from the calibration target 608 defined on the inside surface of the calibration assembly 600. Further, the example flange 622 defines features that hold the arthroscope 408 in a fixed rotational orientation relative to the calibration assembly 600 and the calibration target 608. Various example features to perform the function of holding the arthroscope 408 at the predetermined distance from the calibration target 608, and holding the arthroscope 408 in the fixed rotational orientation relative to the calibration assembly 600, are discussed in greater detail below.

Still referring to FIG. 6, when the arthroscope 408 is telescoped into the example tube 616 for calibration, a volume between the distal end of the arthroscope 408 and the calibration target 608 within the internal volume of the vessel 614 is filled with water, such as saline, to better represent the use case. To that end, the example vessel 614 further defines an aperture or port 626 defined through the wall of the vessel 614 and fluidly coupled to the internal volume. For purposes of calibration, the water may be injected through the port 626. In some cases, the port 626 is associated with a connector or nipple 628. The nipple 628 is coupled to the port 626 (e.g., press fit, threaded connection), and the nipple 628 may provide not only a connection for providing water to the internal volume (e.g., a luer connection), but also may serve the function of a check valve to reduce or prevent water from escaping from the internal volume. It is noted that for purposes of calibration of the arthroscope 408 and camera head 410 (FIG. 4), sufficient water is provided to the internal volume to displace air in the volume between the distal end of the arthroscope 408 and the calibration target 608. More water could be added, which may raise the upper surface of the water to be within the tube 616, but the entire calibration assembly 600 need not be "filled" with water.

Figure 7:
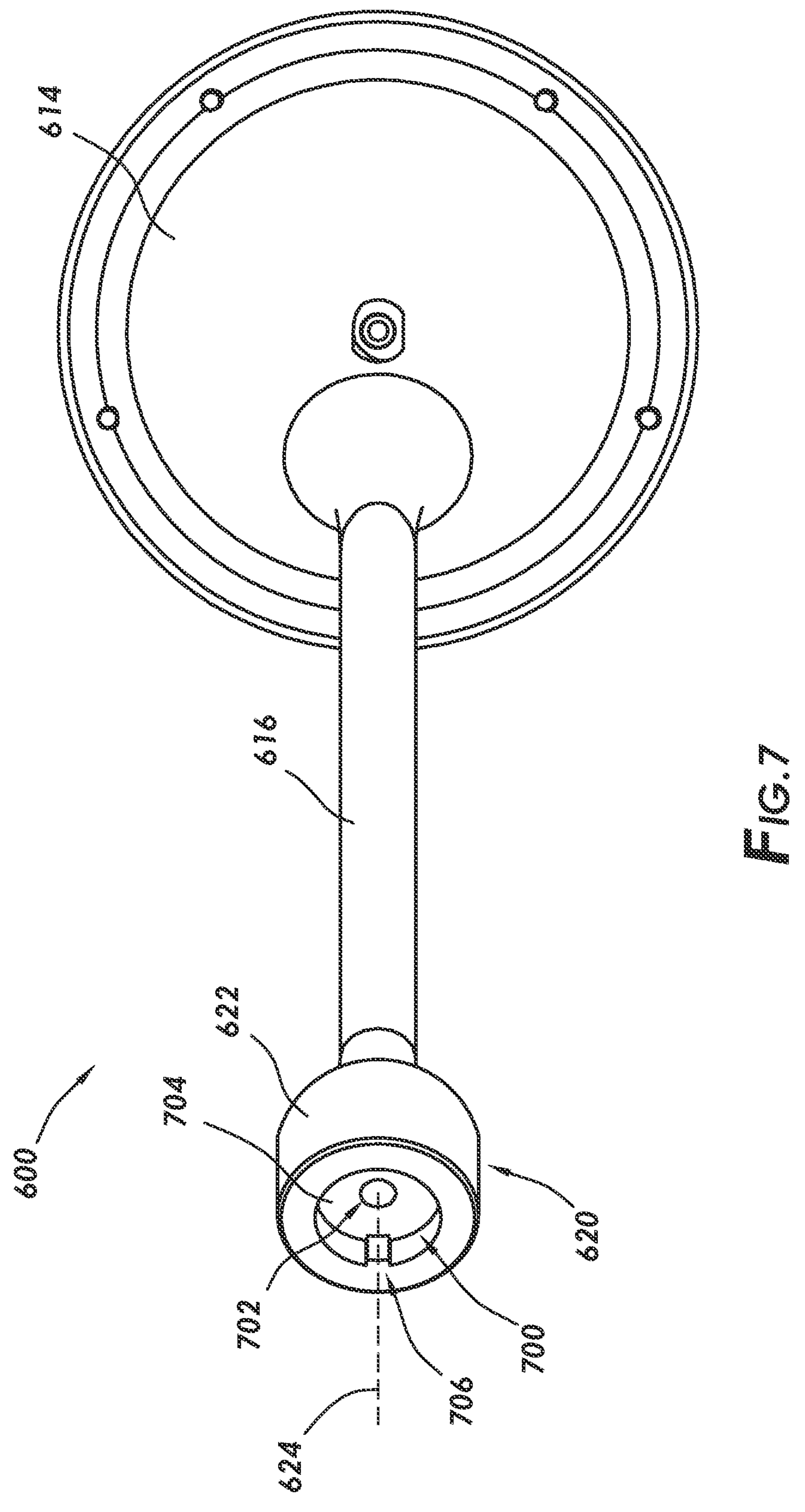
FIG. 7 shows an overhead view of the example calibration assembly in accordance with at least some embodiments.

FIG. 7 shows an overhead view of the example calibration assembly 600. In particular, visible in FIG. 7 is the vessel 614, the tube 616, and the flange 622 on the distal end 620 of the tube 616. Better shown in FIG. 7 are example features defined by the flange 622 that help hold the arthroscope 408. In particular, the flange 622 defines a counterbore 700 having an example circular cross-sectional shape. The counterbore 700 thus defines an inside diameter greater than an inside diameter of the throughbore 702 of the tube 616. In the example shown, the longitudinal central axis 624 of the throughbore 702 is coaxial with the central axis of the counterbore 700. However, in other cases, and depending upon the arrangement of features of the arthroscope and the cross-sectional shape of the counterbore, the alignment of the central axes may differ. The differences in the inside dimensions of the counterbore 700 and throughbore 702 create a shoulder region 704. When the arthroscope 408 (FIG. 6) is telescoped into the tube 616, a feature of the arthroscope 408 abuts the shoulder region 704, thus holding the distal end of the arthroscope 408 at the predetermined distance from the calibration target 608 (FIG. 6). It follows that the shoulder region 704 may be considered an axial retention surface.

The example counterbore 700 further defines a ridge 706 on an inside surface of the counterbore 700. The ridge 706 defines a top and two side surfaces, the ridge 706 projects inward into the counterbore 700, and the ridge 706 runs parallel to the longitudinal central axis 624. The example ridge 706, and particularly the two opposing side surfaces, defines a set of rotational retention surfaces. In particular, the ridge 706 is designed and constructed to fit within a corresponding notch on the arthroscope. When the arthroscope 408 (FIG. 6) is telescoped into the tube 616, in example systems the notch of the arthroscope 408 slides over the ridge 706, and sidewalls of the notch abut the rotational retention surfaces. It follows that the calibration assembly 600, and particularly the rotational retention surfaces defined by the ridge, hold the arthroscope in a fixed rotational orientation relative the calibration target 608 (FIG. 6).

The ridge 706 defining the example rotational retention surfaces is designed and constructed to mate with a corresponding notch of the arthroscope 408 (FIG. 6). However, the rotational retention surfaces may take any suitable form based on the corresponding feature of the arthroscope 408. For example, if the arthroscope 408 defines a ridge rather than a notch, than the corresponding feature associated with the counterbore 700 may be a notch into the flange 622, with the side walls of the notch forming the rotational retention surfaces. Other rotational retention features and surfaces are presented below, including features that both hold the distal end of the arthroscope at the predetermined distance from the calibration target 608 (FIG. 6) and hold the arthroscope in the fixed rotational orientation relative the calibration target 608.

Figure 8:
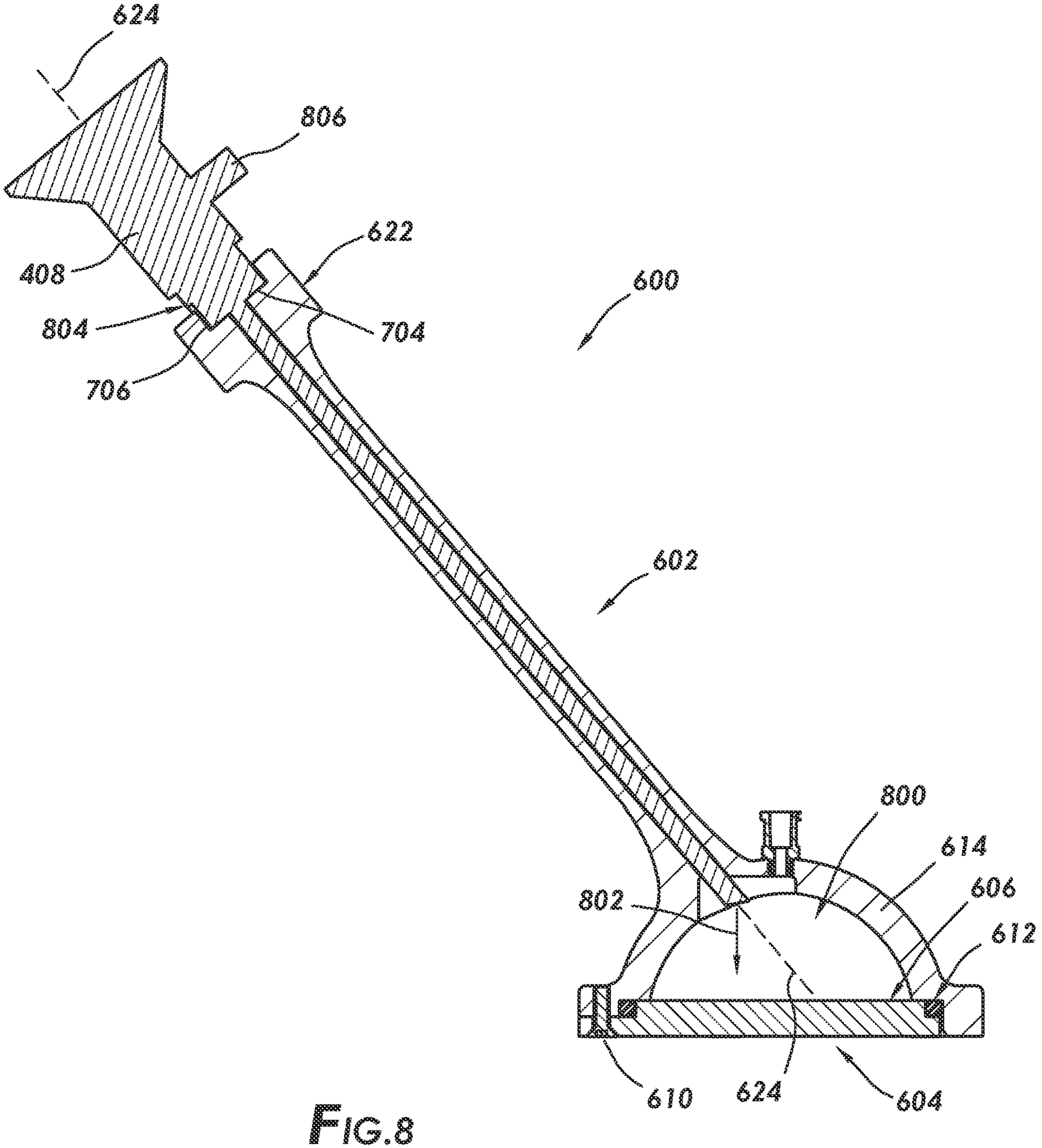
FIG. 8 shows a cross-sectional view of a calibration assembly and arthroscope, in accordance with at least some embodiments.

FIG. 8 shows a cross-sectional view of the example calibration assembly and the arthroscope telescoped into the calibration assembly. In particular, FIG. 8 shows a cross-section of the arthroscope 408 in simplified form, with the internal components of the arthroscope 408 omitted so as not to unduly complicate the figure. Moreover, FIG. 8 shows a cross-section of the example calibration assembly 600, comprising the upper housing 602, the lower housing 604, the O-ring 612, and a single fastener 610 (based on the cut to create the cross-section). Better shown in FIG. 8 is the internal volume 800 defined by the vessel 614 and the inside surface (e.g., the calibration surface 606) of the lower housing 604. The calibration target 608 (FIG. 6) is not visible in the view of FIG. 8.

In the example calibration assembly 600 shown, the calibration surface 606 is a planar surface. Non-planar surfaces may also be used, and when used the shape of the non-planar surface is accounted for during the calibration procedure. In example systems, the longitudinal central axis 624 of the arthroscope 408 intersects the calibration surface 606, and thus intersects the calibration target 608 (FIG. 6). In some cases, the longitudinal central axis 624 forms an acute angle with a vector normal to the calibration surface, the vector normal to the calibration surface not shown so as not to further complicate the figure. In some cases, the longitudinal central axis 624 intersects the calibration target 608 at the center of calibration target 608. In other cases, and as shown, the intersection of the longitudinal central axis 624 is within the calibration target 608 but not at the center of the calibration target. In any event, the arthroscope 408 and camera head 410 (FIG. 4) are able to capture images of the calibration target 608.

As noted above, each arthroscope is designed and constructed to have a particular viewing direction, with the viewing direction quantified as an angle with respect to the longitudinal central axis 624, and the angle measured beyond the distal end of the arthroscope 408. In FIG. 8, the viewing direction 802 is directed toward the calibration surface 606 and thus the calibration target 608 (FIG. 6). In the specific example of FIG. 8, the viewing direction 802 is perpendicular to the calibration surface 606 and thus the calibration target 608. The relationship between the viewing direction 802 and the calibration surface 606 is set, at least in part, by the cut angle on the distal end of the arthroscope 408 that helps form the viewing direction 802. The cut angle on the distal end of the arthroscope 408 has a fixed rotational relationship to the balance of the arthroscope 408, and thus the orientation of the viewing direction 802 is controlled by the location of the rotational retention surfaces defined by the flange 622. In the cross-sectional view of FIG. 8, the rotational retention surfaces are not visible; however, the ridge 706 is visible, along with a portion of the corresponding notch 804 of the example arthroscope 408.

Still referring to FIG. 8, visible in the cross-sectional view is the shoulder region 704. When the arthroscope 408 is telescoped into the calibration assembly 600 as shown, a corresponding feature of the arthroscope 408 contacts or abuts the shoulder region 704. The abutment of the corresponding feature of the arthroscope 408 against the shoulder region 704 limits the distance the arthroscope 408 can be telescoped into the calibration assembly 600. Thus, the combination of the feature of the arthroscope 408 and the shoulder region 704 hold the distal end of the arthroscope 408 at the predetermined distance from the calibration surface 606 and thus the calibration target 608 (FIG. 6). Notice how the light post 806 of the arthroscope 408 does not contact the calibration assembly 600 in the examples discussed to this point.

Figure 9A:
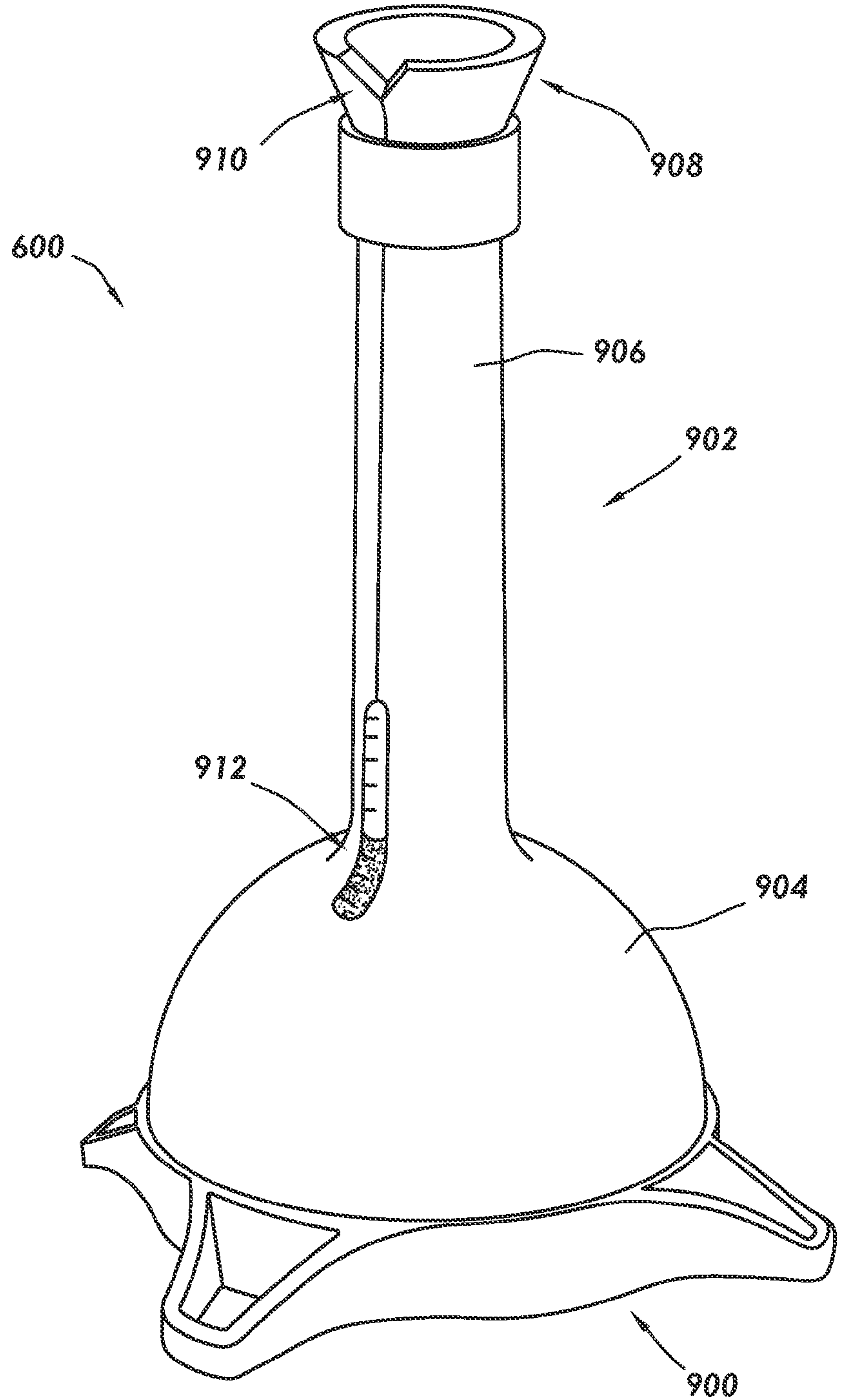
FIG. 9A shows a perspective view of a calibration assembly in accordance with at least some embodiments.

FIG. 9A shows a perspective view of another example calibration assembly. In particular, the calibration assembly 600 of FIG. 9A includes a lower housing 900 and an upper housing 902. Though not visible in FIG. 9A, the lower housing 900 defines a calibration surface with a calibration target. The upper housing 902 defines a vessel 904 and a tube 906. As before, the vessel 904 together with the lower housing 900 define an internal volume. Further as before, the tube 906 defines a throughbore that is fluidly coupled to the internal volume within the vessel 904. The example calibration assembly 600 of FIG. 9A further defines a flange 908 on the distal end of the tube 906.

The arrangement of the tube 906 in relationship to the vessel 904 and lower housing 900 is different than the calibration assembly 600 of FIG. 6. In particular, in the example of FIG. 9A the longitudinal central axis of the throughbore of the tube 906 is designed and constructed to intersect the calibration target (not visible) such that the longitudinal central axis of the tube 906 is perpendicular to the calibration surface and thus the calibration target. More particularly still, in the example arrangement of FIG. 9A the longitudinal central axis of the throughbore of the tube 906 intersects the center of the calibration target, though other non-center intersections are contemplated. It follows from the arrangement of the tube 906 and vessel 904 that the example calibration assembly 600 of FIG. 9A may be designed and constructed for calibration of an arthroscope with a zero degree viewing angle.

FIG. 9A further shows another mechanisms to hold the distal end of the arthroscope at the predetermined distance from the calibration target, and to hold the arthroscope at a fixed rotational orientation relative to the calibration target. In particular, the example flange 908 defines features that provide both the axial retention (e.g., axial along the longitudinal central axis of the arthroscope and/or throughbore of the tube 906) and rotational retention surfaces. More particularly still, the example flange 908 defines a notch 910. The notch 910 defines a channel with a closed bottom, an open top, and two side walls. The channel formed by the notch 910 cuts across the flange 908, and in the example shown a channel line formed in the direction of the notch intersects the longitudinal central axis of the throughbore of the tube 906. In some cases (not specifically shown), the channel line is perpendicular to the longitudinal central axis of the throughbore of the tube 906.

In use, the arthroscope 408 (FIG. 4) is telescoped into the tube 906, and the light post 420 (FIG. 4) is placed in the notch 910. The side walls of the notch 910 hold the arthroscope in a fixed rotational orientation with respect to the calibration assembly 600. Moreover, the side walls (and a bottom wall if the notch is rectangular), hold the distal end of the arthroscope at the predetermined distance from the calibration target. The notch 910 may thus be considered both an axial retention surface and a rotational retention surface.

Further visible in FIG. 9A is sight gauge 912. To the extent that the material that forms the upper housing 902 is otherwise opaque, the example sight gauge 912 is constructed of a clear or transparent material that enables the user to view the elevation of the interface between air and water within the calibration assembly 600, and thus to determine the depth of water within the calibration assembly 600. The surgeon may use the sight gauge during the setup procedures to ensure that sufficient water is provided to the vessel 904, such as to ensure that the water level is above the distal end of the arthroscope.

FIG. 9A thus shows several alternative arrangements, including the alternative arrangement of the tube 906 to the vessel 904 and lower housing 900, an alternative arrangement of rotational retention features to hold the arthroscope in a fixed rotational orientation, an alternative arrangement of axial retention features to hold the distal end of the arthroscope at the predetermined distance from the calibration target, and an example sight gauge. It is noted, however, that these features are not limited to the calibration assembly 600 of FIG. 9A. Now understanding the calibration assembly, one of ordinary skill would recognize that the various features may be mixed and matched as desired. For example, the notch 910 forming the dual role of axial and rotational retention feature could be used with the tube and vessel arrangement of FIGS. 6-8. Oppositely, the flange 622 of the calibration assembly of FIGS. 6-8 may be used as the flange of the calibration assembly of FIG. 9A. Similarly, the sight gauge could be implemented in the calibration assembly 600 of FIGS. 6-8, and fill mechanics could be implemented in the calibration assembly of FIG. 9A.

Figure 9B:
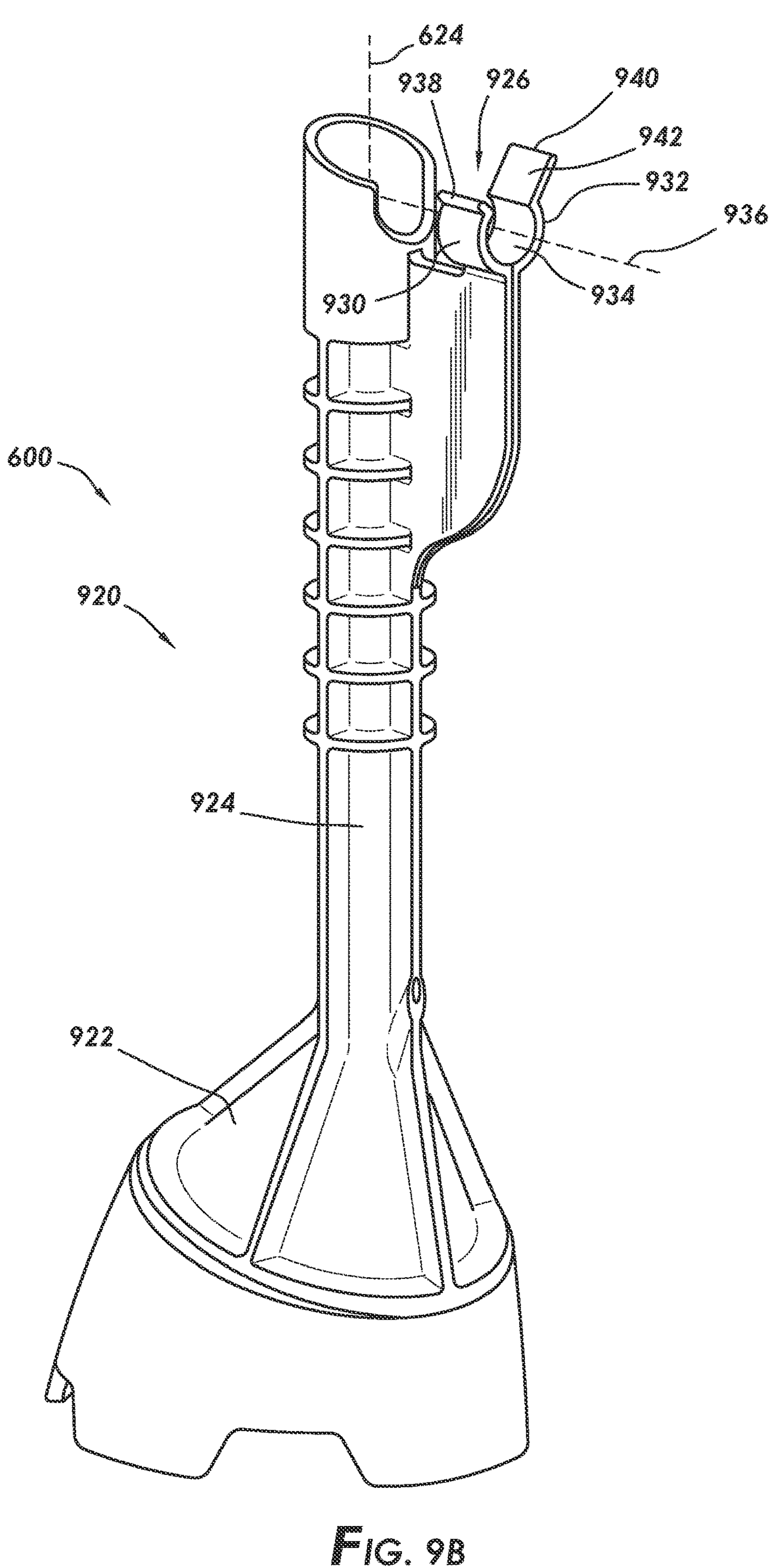
FIG. 9B shows a perspective view of a calibration assembly in accordance with at least some embodiments.

FIG. 9B shows a perspective view of another example calibration assembly. In particular, the calibration assembly 600 of FIG. 9B includes an outer housing 920 and a lower housing that is not visible in FIG. 9B. As discussed more below, the lower housing defines or supports a calibration surface with a calibration target. The outer housing 920 defines a vessel 922 and a tube 924. As before, the vessel 922 together with the lower housing define an internal volume. Further as before, the tube 924 defines a throughbore that is fluidly coupled to the internal volume within the vessel 922. The example calibration assembly 600 of FIG. 9B further defines a light-post snap or clip 926 disposed at the distal end of the tube 924.

In the example of FIG. 9B the longitudinal central axis of the throughbore of the tube 924 is designed and constructed to intersect the calibration target (not visible) such that the longitudinal central axis of the tube 924 forms an acute angle to the calibration surface and thus the calibration target. It follows from the arrangement of the tube 924 and vessel 922 that the example calibration assembly 600 of FIG. 9B may be designed and constructed for calibration of an arthroscope with a non-zero viewing angle. Moreover, the calibration assembly 600 of FIG. 9B may be more stable when, for example, placed on a table for use or later re-use.

FIG. 9B further shows another mechanisms to hold the distal end of the arthroscope at the predetermined distance from the calibration target, and to hold the arthroscope at a fixed rotational orientation relative to the calibration target. In particular, the example clip 926 defines features that provide both the axial retention (e.g., axial along the longitudinal central axis of the arthroscope and/or throughbore of the tube 924) and rotational retention surfaces. More particularly still, the example clip 926 defines a first wall or arm 930 and a second wall or arm 932, though the arms 930 and 932 may be integrally formed components. The arms 930 and 932 define an interior surface 934 that is complementary to the light post 420 (FIG. 4). In particular, the interior surface 934 defines a semicircular surface with a central axis 936 that intersects the longitudinal central axis 624 of the tube 924. In an example case, the central axis 936 is perpendicular to the longitudinal central axis 624. The example arm 930 defines a slide 938 with an outer surface (not visible in FIG. 9B) that directs a light post 420 into the volume defined by the interior surface 934. Moreover, the arm 932 defines a slide/release 940 with an outer surface 942 that directs the light post 420 into the volume defined by the interior surface 934. During installation of the arthroscope 408 (FIG. 4) into the calibration assembly 600 of FIG. 9B, as the elongate shaft of the arthroscope 408 telescopes into the tube 924, the light post 420 abuts the outer surface of the slide 938 and outer surface 942 of the slide/release 940. Further pressure causes the arms 930 and 932 to flex open slightly, enabling light post 420 to snap or clip into the clip 926. Thus, the clip 926 holds the arthroscope 408 in a fixed rotational orientation with respect to the calibration assembly 600, and the clip 926 holds the distal end of the arthroscope 408 at the predetermined distance from the calibration target. The clip 926 may thus be considered an axial retention surface and a rotational retention surface.

Figure 9C:
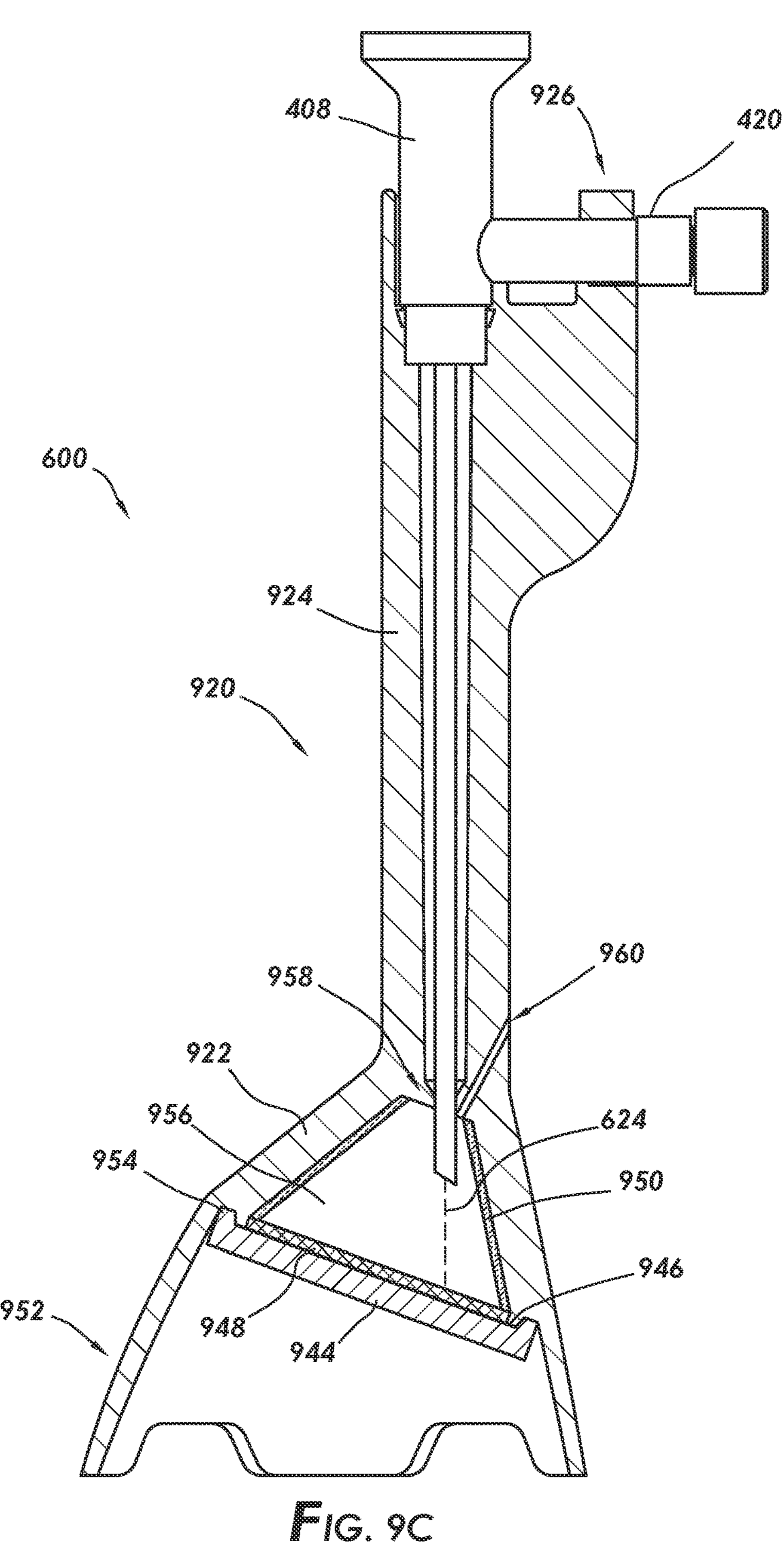
FIG. 9C shows a cross-sectional view of a calibration assembly and arthroscope, in accordance with at least some embodiments.

FIG. 9C shows a cross-sectional view of a calibration assembly and arthroscope. In particular, FIG. 9C shows the arthroscope 408 in simplified form. Moreover, FIG. 9C shows a cross-section of the example calibration assembly 600, comprising the outer housing 920, a lower housing 944 defining a calibration surface 946, a calibration target 948, and an optional reflective surface 950. The example outer housing 920 defines not only a portion of the vessel 922 and the tube 924, but also a stand 952 that enables the calibration assembly 600 of FIG. 9C to rest up on a horizontal surface both in use and between uses. In the example, the lower housing 944 is coupled to the outer housing 920 and sealed in any suitable form, such as by friction welding the lower housing 944 to the outer housing 920 at the interface point 954. Better shown in FIG. 9C is the internal volume 956 defined by the vessel 922 and the inside surface (e.g., the calibration surface 946) of the outer housing 920. The pattern of the calibration target is not visible in the view of FIG. 9C. In one example, the calibration target 948 is a polymer specifically selected to enable laser marking to create the calibration pattern, and then the calibration target 948 is placed on the calibration surface 946 and held in place by other structural components. In other cases, the calibration target may be a pre-printed flexible material that is coupled (e.g., adhered) to the calibration surface 946 prior to the lower housing being assembled with the remaining components.

In the example calibration assembly 600 of FIG. 9C, the calibration surface 946 is a planar surface. Non-planar surfaces may also be used, and when used the shape of the non-planar surface is accounted for during the calibration procedure. In example systems, the longitudinal central axis 624 of the arthroscope 408 intersects the calibration surface 946, and thus intersects the calibration target. In some cases, the longitudinal central axis 624 forms an acute angle with a vector normal to the calibration surface, the vector normal to the calibration surface not shown so as not to further complicate the figure. In some cases, the longitudinal central axis 624 intersects the calibration target 948 at the center of calibration target 948. In other cases, and as shown, the intersection of the longitudinal central axis 624 is within the calibration target 948 but not at the center of the calibration target. In any event, the arthroscope 408 and camera head 410 (FIG. 4) are able to capture images of the calibration target 948.

As noted above, each arthroscope is designed and constructed to have a particular viewing direction, with the viewing direction quantified as an angle with respect to the longitudinal central axis 624, and the angle measured beyond the distal end of the arthroscope 408. In FIG. 9C, the viewing direction (not specifically delineated) is directed toward the calibration surface 948 and thus the calibration target 948. In the specific example of FIG. 9C, the viewing direction may be perpendicular to the calibration surface 946 and thus the calibration target 948. The relationship between the viewing direction and the calibration surface 946 is set, at least in part, by the cut angle on the distal end of the arthroscope 408 that helps form the viewing direction. The cut angle on the distal end of the arthroscope 408 has a fixed rotational relationship to the balance of the arthroscope 408 (e.g., the light post 420), and thus the orientation of the viewing direction is controlled by the location of the rotational retention surfaces defined by the clip 926. In the cross-sectional view of FIG. 9C, the rotational retention surfaces are not visible.

Still referring to FIG. 9C, when the arthroscope 408 is telescoped into the calibration assembly 600 of FIG. 9C as shown, the light post 420 contacts or abuts the inside surface of the clip 926. The abutment of the light post 420 with the clip 926 limits the distance the arthroscope 408 can be telescoped into the calibration assembly 600. Moreover, the rotational retention features implemented by the clip 926 against the light post 420 orient and hold the viewing direction relative to the calibration target 928. The example calibration assembly 600 further defines, at the transition from the tube 924 to the internal volume 956, a neck or flange 958. The flange 958 defines a diameters that forms a slip fit with the outside surface of arthroscope 408. That is, while a majority of the inside surface of the tube 924 has an inside diameter greater than the outside diameter of the arthroscope 408 (e.g., 1 to 5 mm), the inside diameter at the location of the flange 958 is smaller to enable the arthroscope 408 to telescope through the flange, yet hold the distal end of the arthroscope 408 in a fixed position relative to the calibration target 948. In one example, the inside diameter of the flange 958 may be between 0.1 and 0.5 mm larger than the outside diameter of the portion of the arthroscope that telescopes through the flange. In order to have a vent path for fluid within the internal volume 956 displaced by the arthroscope, the example calibration assembly of FIG. 9C also includes a vent aperture 960.

FIGS. 9A-9C thus show several alternative arrangements, including the alternative arrangement of the tube to the vessel and lower housing, and an alternative arrangement of axial and rotational retention features to hold the arthroscope in a fixed rotational orientation. It is noted, however, that these features are not limited to the calibration assemblies 600 of FIG. 9A-9C. Now understanding the calibration assembly, one of ordinary skill would recognize that the various features may be mixed and matched as desired. For example, the clip 926 may be used with the calibration assemblies of FIGS. 6-9A. Oppositely, the flange 622 of the calibration assembly of FIGS. 6-8 may be used as the flange of the calibration assembly of FIGS. 9B-9C. Similarly, the sight gauge of FIG. 9A could be implemented in the calibration assembly 600 of FIGS. 6-8 or the calibration assembly of FIGS. 9B-9C, and fill mechanics of FIGS. 6-8 could be implemented in the calibration assemblies of FIG. 9A-9C.

Figure 9D:
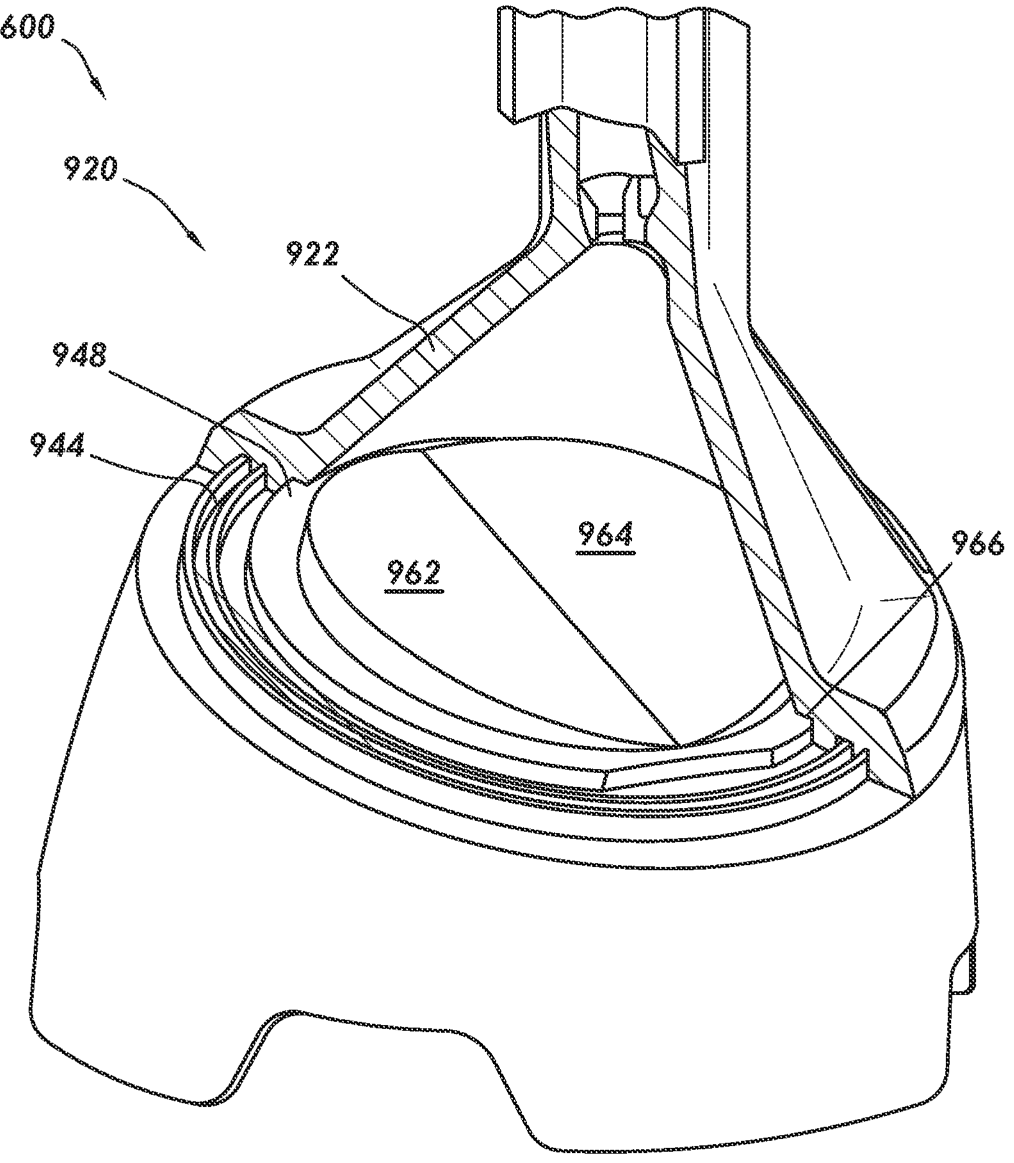
FIG. 9D shows a partial perspective, cut-away view of a calibration assembly, in accordance with at least some embodiments.

The calibration targets of FIGS. 6-8 and 9A-9C all show to be planar. However, in other cases the calibration targets need not be planar so long as the shape of the calibration target is known in advance. FIG. 9D shows a partial perspective, cut-away view of an example calibration assembly 600. In particular, visible in FIG. 9D is the vessel 922 cut away to show a portion of the lower housing 944 and an example calibration target 948. In this case, however, the calibration target 948 defines a first portion 962 defining a first plane, and a second portion 964 defining a second plane, and where the first and second planes form an acute angle on the calibration-target side (e.g., a V-shape). Not show in FIG. 9D is the actual calibration pattern, which may take any suitable shape or set of shapes. The view of FIG. 9D better shows that the outer housing 920 may define a shoulder region 966 that holds the example calibration target 948 in place. Further, FIG. 9D shows an example in which the reflective surface (e.g., reflective surface 950 of FIG. 9C) is omitted from the inside surface of the vessel 922. While the calibration target 948 of FIG. 9D shows two planes defining an acute angle between them on the calibration-target side, in other cases a calibration target may have a first portion defining a first plane, and a second portion defining a second plane, and where the first and second planes form an obtuse angle on the calibration-target side (e.g., an inverted V-shape). In yet still further cases, the calibration target may comprise three or more planes in any suitable arrangement.

Before proceeding to a discussion of use the calibration assemblies, a few points are in order. While FIGS. 6-8 and 9A-9D show several examples, any vessel (e.g., box, pouch, or bag) that holds water and which may contain a calibration target may be used as the calibration assembly. The specification now turns to an example use of the calibration assembly as part of the calibration procedures.

Returning to FIG. 4, in operation as part of calibration procedure, the camera head 410 is attached to the arthroscope 408. The camera head 410 is communicatively coupled to the surgical controller 418, and the light post of the arthroscope 408 is optically coupled to a light output port of the surgical controller 418. The arthroscope 408 is telescoped into the calibration assembly 428. Water is placed within the internal volume of the calibration assembly 428, displacing the air between the calibration target and the distal end of the arthroscope 408. The surgeon may then trigger a calibration procedure, such as by interacting with the surgical controller 418 (e.g., by way of a tablet-type portable electronic device communicatively coupled to the surgical controller 418). Once the calibration procedure begins, the example calibration may comprise capturing a plurality of images of the calibration target, each image captured at a unique rotational relationship between the camera head 410 and the arthroscope 408, and the unique rotational relationships relative to the longitudinal central axis of the arthroscope 408. More particularly, capturing the plurality of images may comprise: capturing a first image of the calibration target at a first rotational orientation between the arthroscope 408 and the camera head 410, the capturing by the surgical controller 418 by way of the capture array of the camera head 410; and then capturing a second image of the calibration target at a second rotational orientation between the arthroscope 408 and the camera head 410, such as by turning the camera head 410 relative to the arthroscope 408 whilst the arthroscope 408 remains in a fixed rotational orientation with respect to the calibration assembly; and then capturing a third image of the calibration target at a third rotational orientation between the arthroscope 408 and the camera head 410, again such as by turning the camera head 410 relative to the arthroscope 408. In one example, the camera head 410 may be turned 120 rotational degrees between each image capture when three images are used. If a greater number of images are to be captured, the amount the camera head 410 is turned between each image capture is reduced accordingly.

Based on the images captured, the surgical controller 418 may calculate a characterization function that characterizes optical distortion between the calibration target and the capture array of the camera head 410. The distortion includes not only distortion introduced in the optics of the camera head 410 (e.g., focus assembly), but also any optical distortion associated with the optical path through the arthroscope 408, and any optical distortion introduced by the water (e.g., again, mimicking the situation within the surgical site). Further still, the surgical controller 418 may use the captured images to create the characterization function as a calibration for determining orientation of fiducial markers by way of the arthroscope 408, in this case having a single optical path through the arthroscope. The specification now turns to registration of the bone model, and a human-in-the-loop verification of the registration.

Model Registration and Human-In-the-Loop Registration Verification

The next example step in the intraoperative procedure is the registration of the bone model(s). That is, during the planning stage, imaging (e.g., MRI) of the knee takes place, including the relevant anatomy like the lower portion of the femur, the upper portion of the tibia, and the articular cartilage. The imaging can be segmented such that a volumetric model or three-dimensional model of the anatomy is created. More specifically to the example of ACL repair, and specifically selecting a tunnel path through the femur, a three-dimensional bone model of the lower portion of the femur is created during the planning.

During the intraoperative repair, the three-dimensional bone models are provided to the surgical controller 418. Again using the example of ACL repair, and specifically computer-assisted navigation for tunnel paths through the femur, the three-dimensional bone model of the lower portion of the femur is provided to the surgical controller 418. Thus, the surgical controller 418 receives the three-dimensional bone model, and assuming the arthroscope 408 is inserted into the knee by way of a port through the patient's skin, the surgical controller 418 also receives video images of the femur. In order to relate the three-dimensional bone model to the images received by way of the arthroscope 408 and camera head 410, the surgical controller 418 registers the three-dimensional bone model to the images of the femur received by way of the arthroscope 408 and camera head 410.

In accordance with example methods, a fiducial marker or bone fiducial (e.g., bone fiducial 502 of FIG. 5) is attached to the femur. The bone fiducial placement is such that the bone fiducial is within the field of view of the arthroscope 408, but in a location spaced apart from the expected tunnel entry/exit point through the lateral condyle. More particularly, in example cases the bone fiducial is placed within the intercondylar notch superior to or above the expected location of the tunnel through lateral condyle.

Figure 10:
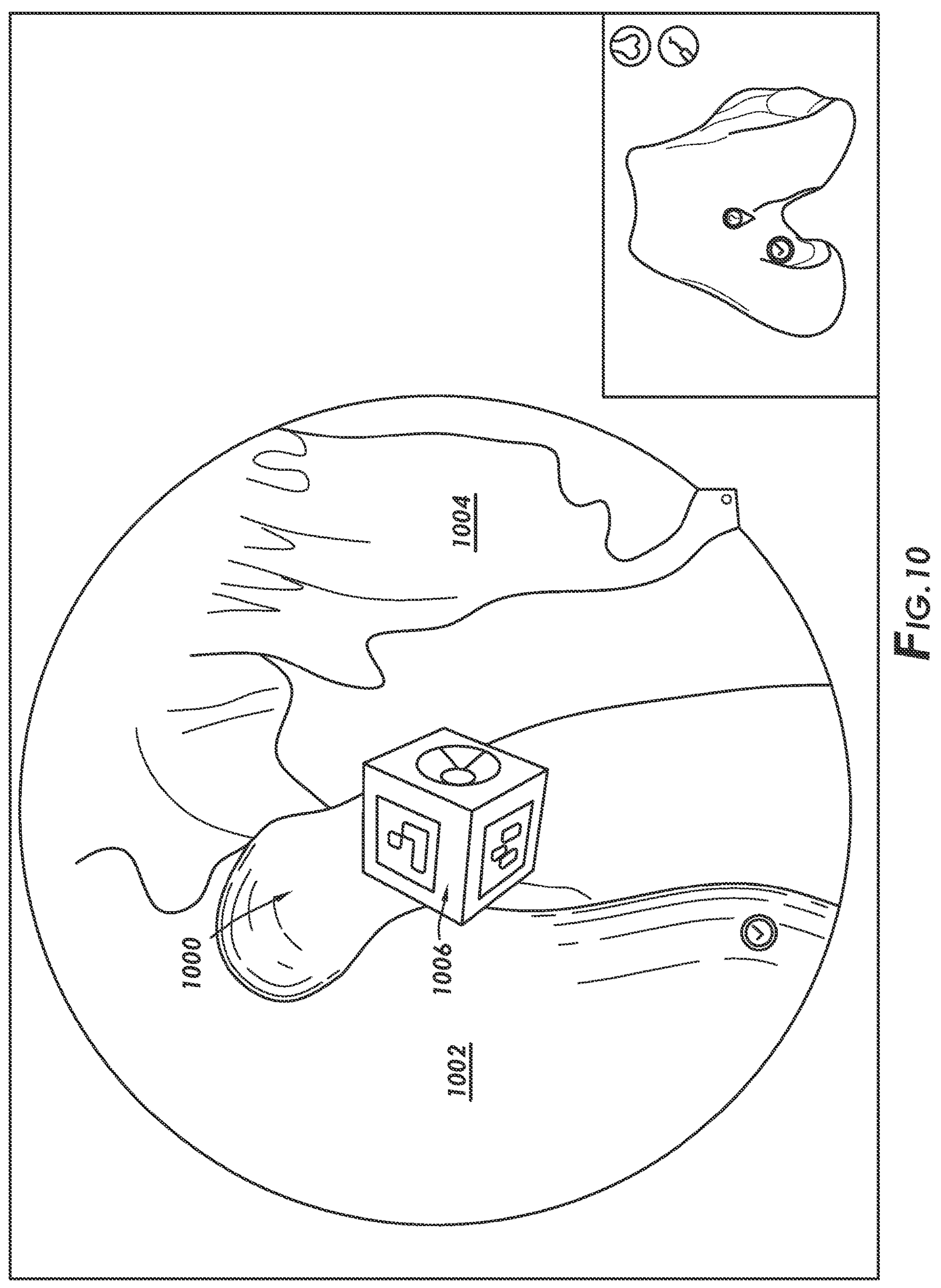
FIG. 10 is an example video display showing portions of a femur and having visible therein a bone fiducial, in accordance with at least some embodiments.

FIG. 10 is an example video display showing portions of a femur and a bone fiducial. The display may be shown, for example, on the display device 414 (FIG. 4) associated with the device cart 402 (FIG. 4), or any other suitable location. In particular, visible in FIG. 10 is a femoral notch or intercondylar notch 1000, a portion of the lateral condyle 1002, a portion the medial condyle 1004, and an example bone fiducial 1006. The bone fiducial 1006 is a fiducial comprising a cube member. Of the six outer faces of the cube member, the bottom face is associated with an attachment feature (e.g., a screw). The bottom face will be close to or abut the bone when the bone fiducial 1006 is secured in place, and thus will not be visible in the view of the arthroscope 408 (FIG. 4). The outer face opposite the bottom face includes a placement feature used to hold the bone fiducial 1006 prior to placement, and to attach the bone fiducial 1006 to the underlying bone. Of the remaining four outer faces of the cube member (only two of the remaining faces are visible), each of the four outer faces has a machine-readable pattern thereon, and in some cases each machine-readable pattern is unique. Once placed, the bone fiducial 1006 represents a fixed location on the outer surface of the bone in the view of the arthroscope 408, even as the position of the arthroscope 408 is moved and changed relative to the bone fiducial 1006. Initially, the location of the bone fiducial 1006 with respect to the three-dimensional bone model is not known to the surgical controller 418, hence the need for the registration of the three-dimensional bone model.

In or order to relate or register the bone visible in the video images to the three-dimensional bone model, the surgical controller 418 (FIG. 4) is provided and thus receives a plurality of locations of an outer surface of the bone. For example, the surgeon may touch a plurality of locations using the touch probe 504 (FIG. 5). As previously discussed, the touch probe 504 comprises a probe fiducial 506 (FIG. 5) visible in the video images captured by the arthroscope 408 (FIG. 4) and camera head 410 (FIG. 4). The physical relationship between the distal end of the touch probe 504 and the probe fiducial 506 is known by the surgical controller 418, and thus as the surgeon touches each of the plurality of locations on the outer surface of the bone, the surgical controller 418 gains an additional "known" locations of the outer surface of the bone relative to the bone fiducial 1006. Given that the touch probe 504 is a relatively inflexible instrument, in other examples the tracking of the touch probe 504 may be by optical tracking of an optically-reflective array outside the surgical site (e.g., tracking by the camera 412 (FIG. 4)) yet attached to the portion of the touch probe 504 inside the surgical site.

In some cases, particularly when portions of the outer surface of the bone are exposed to view, receiving the plurality of locations of the outer surface of the bone may involve the surgeon "painting" the outer surface of the bone. "Painting" is a term of art that does not involve application of color or pigment, but instead implies motion of the touch probe 504 when the distal end of the touch probe 504 is touching bone.

Figure 11:
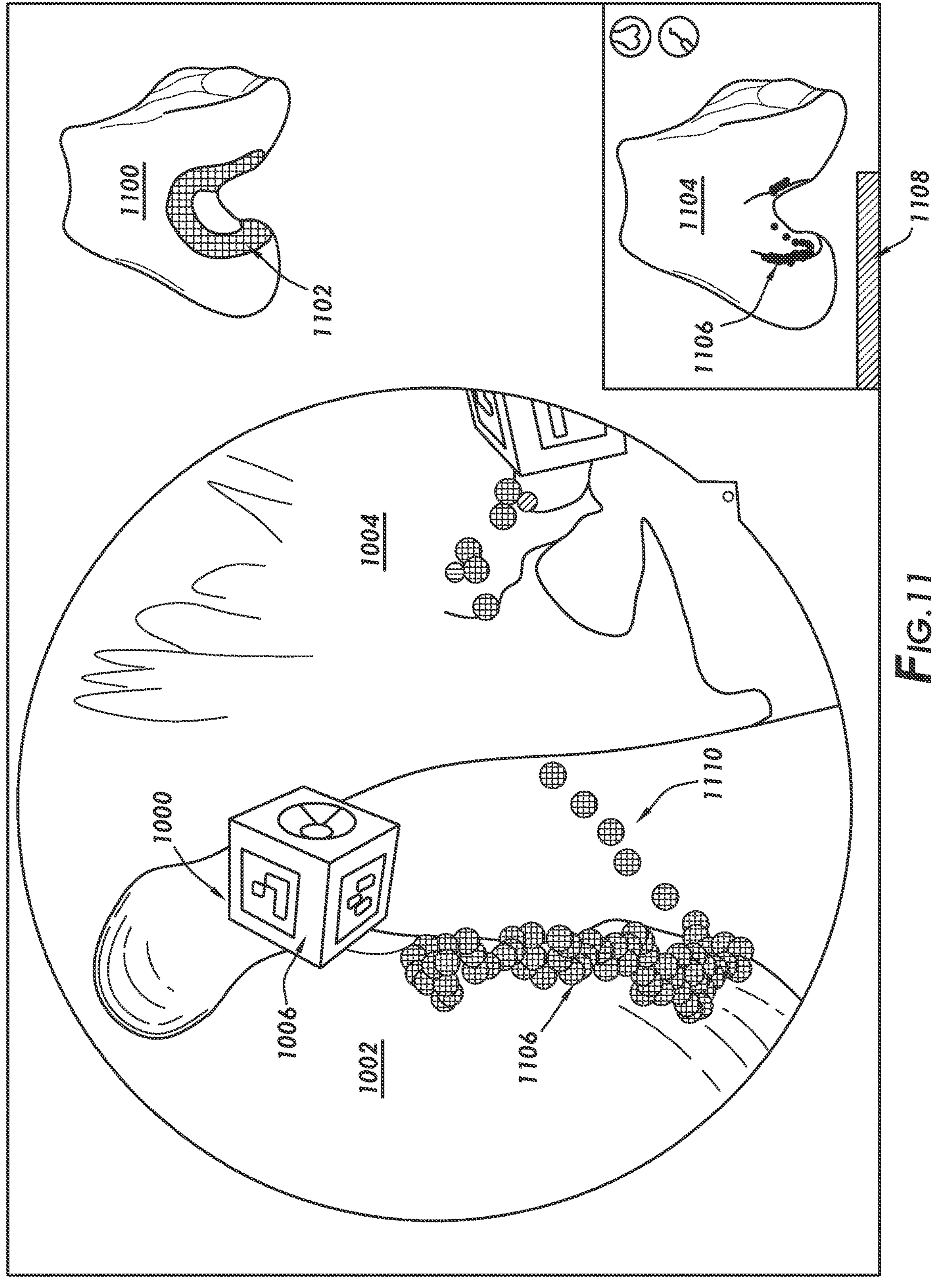
FIG. 11 is an example video display showing portions of a femur and a bone fiducial during a registration procedure, in accordance with at least some embodiments.

FIG. 11 is an example video display showing portions of a femur and a bone fiducial during a registration procedure. The display may be shown, for example, on the display device 414 (FIG. 4) associated with the device cart 402 (FIG. 4), or any other suitable location. In particular, visible in the main part of the display of FIG. 11 is the intercondylar notch 1000, a portion of the lateral condyle 1002, a portion the medial condyle 1004, and the example bone fiducial 1006. Shown in the upper right corner of the example display is a depiction of the bone, which may be a rendering 1100 of the bone created from the three-dimensional bone model. Shown on the rendering 1100 is a recommended area 1102, the recommended area 1102 being portions of the surface of the bone to be painted as part of the registration process. Shown in the lower right corner of the example display is a depiction of the bone, which again may be a rendering 1104 of the bone created from the three-dimensional bone model. Shown on the rendering 1104 are a plurality of locations 1106 of the bone model that have been correlated to the locations on the outside surface of the bone as part of the registration process. Further shown in the lower right corner of the example display is progress indicator 1108, showing the progress of providing and receiving of locations on the bone. The example progress indicator 1108 is a horizontal bar having a length that is proportional to the number of locations received. In the example case, the progress indicator 1108 grows or extends in length toward from a fixed location on the left and toward the right, but any suitable graphic or numerical display showing progress may be used (e.g., 0% to 100%).

Referring to both the main display and the lower right rendering, as the surgeon touches and/or paints the outer surface of the bone within the images captured by the arthroscope 408 (FIG. 4) and camera head 410 (FIG. 4), the surgical controller 418 (FIG. 4) receives the locations on the bone, and displays each location both within the main display as dots or locations 1106, and within the rendering shown in the lower right corner. More specifically, the example surgical controller 418 overlays indications of received locations 1106 on the display of the images captured by the arthroscope 408 and camera head 410, and in the example case shown, also overlays indications of received locations 1106 on the rendering 1104 of the bone model. Moreover, as the number of received locations 1106 increases, the surgical controller 418 also updates the progress indicator 1108.

Still referring to FIG. 11, in spite of the diligence of the surgeon, not all locations received by the surgical controller 418 (FIG. 4) based on the surgeon's movement of the touch probe 504 (FIG. 5) result in valid locations on the surface of the bone. In the example of FIG. 11, as the surgeon moved the touch probe 504 from the inside surface of the lateral condyle 1002 to the inside surface of the medial condyle 1004, the surgical controller 418 received several locations 1110 that likely represent locations in the three-dimensional coordinate space of the view of the arthroscope at which the distal end of the touch probe 504 was not in contact with the bone. Nevertheless, and as shown in the lower right corner, those locations 1110 may be incorrectly attributed to locations on the outer surface of the bone. It follows that correlating the three-dimensional bone model to the bone visible in the three-dimensional coordinate space in the view of the arthroscope is not necessarily a fully determinative procedure. Some received locations may need to be ignored in the correlation, some received locations that should be used may be ignored, and other received locations that should be ignored may nonetheless be used, which may result in an incorrect correlation between the three-dimensional bone model and the bone visible in the images as anchored by the bone fiducial 1006. The specification now turns to human-in-the-loop registration verification.

Figure 12:
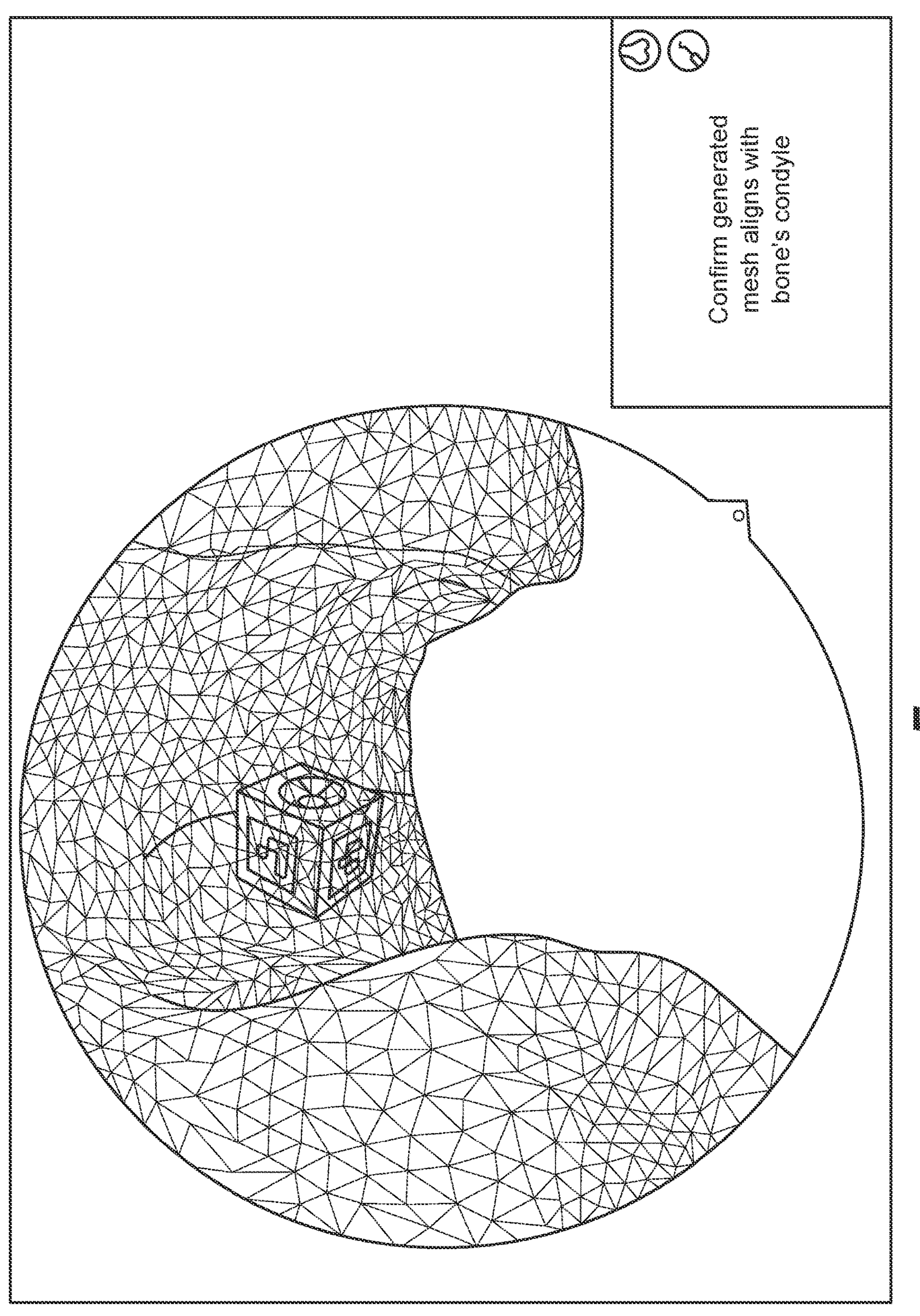
FIG. 12 is an example video display during a registration procedure showing portions of a femur, a bone fiducial, and an overlaid representation of the three-dimensional bone model, in accordance with at least some embodiments.

FIG. 12 is an example video display during a registration procedure showing portions of a femur, a bone fiducial, and an overlaid representation of the three-dimensional bone model. The display may be shown, for example, on the display device 414 (FIG. 4) associated with the device cart 402 (FIG. 4), or any other suitable location. In order to address potential invalid registrations between the three-dimensional bone model and the bone visible in the images, in example methods and systems an initial registration between the bone visible in the video images and the three-dimensional bone model is verified using a human-in-the-loop process. More particularly, in example cases, after receiving the plurality of locations of an outer surface of the bone visible in the images and performing an initial registration to the three-dimensional bone model, the surgical controller 418 displays a representation of the three-dimensional bone model overlaid on portions of the bone visible in the video images, the displaying and overlaying on the display device 414, or other suitable location. That is, the example surgical controller 418 overlays a representation of the three-dimensional bone model (e.g., by way of a polygon mesh, or mesh model) on the display of the images captured by the arthroscope 408 and camera head 410, wherein the rotational and translational alignment of the three-dimensional bone model is correlated to the bone visible in the video images as anchored by the bone fiducial 1006.

The surgeon, in turn, visually studies the overlaid representation of the three-dimensional bone model relative to the underling bone visible in the video images to determine whether the registration process was correct. More particularly, the surgeon visually compares the overlaid representation of the three-dimensional bone model to the portion of the bone visible in the video images to determine whether the three-dimensional bone model sufficiently matches the bone visible in the video images. Much like the registration process itself, the human-in-the-loop verification of registration is a non-deterministic exercise. Slight variances between the three-dimensional bone model and the bone visible in the video images may be tolerated, yet nevertheless the registration process may be considered correct in the sense that the three-dimensional bone model may be reliably used to help guide placement of the tunnel path (e.g., here the femoral tunnel path), or assist the surgeon in intraoperative changes to the planned-tunnel path. In such cases, the surgeon may provide the surgical controller 418, and the surgical controller 418 may thus receive, an indication that the three-dimensional bone model is correctly registered to the bone visible in the video images.

On the other hand, if the overlay of the three-dimensional bone model shows misalignment with the bone visible in the video images, the surgeon may elect to restart the registration process, such as by providing to the surgical controller 418, and the surgical controller 418 receiving again, a plurality of locations of the outer surface of the bone. The surgical controller 418 may then perform anew the registration procedure. In other cases, the surgeon may elect to provide additional locations on the outer surface of the bone, and the surgical controller 418 may then perform the registration procedure with the both original locations received and the additional locations received after the overlay process. The process repeats until the surgeon approves the registration. The specification now turns to intraoperative tunnel path planning.

Tunnel Path Planning

Using the three-dimensional bone model an operative plan is created that comprises a planned-tunnel path through the bone, including locations of the apertures into the bone that define the ends of the tunnel. In some cases, however, the surgeon may elect not to use planned-tunnel path, and thus elect not use the planned entry location, exit location, or both. Such an election can be based any of a number of reasons. For example, intraoperatively the surgeon may not be able to access the entry location for the planned-tunnel path, and thus may need to move the entry location to ensure sufficient access. As another example, during the intraoperative procedure the surgeon may determine that the planned tunnel entry location is misaligned with the attachment location of the native ACL to the femur. Further still, during the intraoperative procedure the surgeon may determine the tunnel entry location is too close to the posterior wall of the femur, increasing the likelihood of a bone chip sometimes referred to as a "back wall blowout." Regardless of the reason for the election to change the tunnel path, in example systems the surgical controller 418 enables the surgeon to intraoperatively select a revised-tunnel entry, a revised-tunnel exit (if needed), and thus a revised-tunnel path through the bone.

Figure 13:
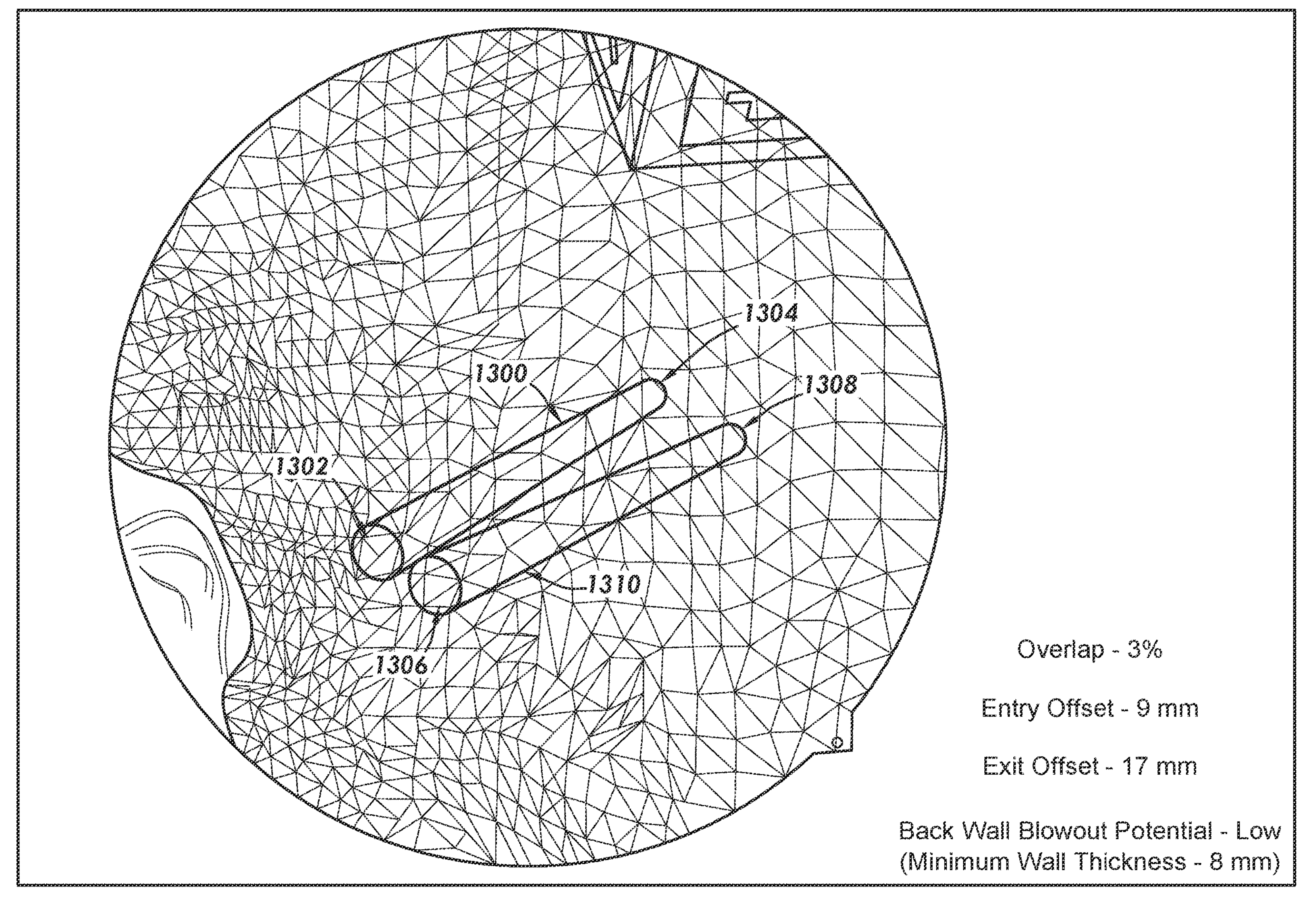
FIG. 13 is an example video display showing intraoperative changes to the tunnel path, in accordance with at least some embodiments.

FIG. 13 is an example video display showing intraoperative changes to the tunnel path, in accordance with at least some embodiments. The display may be shown, for example, on the display device 414 (FIG. 4) associated with the device cart 402 (FIG. 4), or any other suitable location. In particular, FIG. 13 shows a portion of the bone in the video images as captured by the arthroscope 408 (FIG. 4) overlaid with the mesh model of the three-dimensional bone model and a selected planned-tunnel path 1300 comprising a planned-tunnel entry 1302 and a planned-tunnel exit 1304. However, for any number of reasons, the surgeon may elect to modify the tunnel entry location and/or the tunnel exit location, and thus modify the planned-tunnel path. Thus, the surgeon may provide to the surgical controller 418 (FIG. 4), and thus the surgical controller 418 may receive, a revised-tunnel entry location or just revised-tunnel entry 1306. Providing the revised-tunnel entry 1306 may comprise the surgeon touching the proposed location on the bone shown in the video images with a tracked tool, such as the touch probe 504 (FIG. 5) or the aimer 426 (FIG. 4). In some cases, the surgeon may select the revised-tunnel entry 1306 based solely on what the surgeon sees of the bone shown in the video images. As a more specific example, the surgeon may select and provide the revised-tunnel entry 1306 based on a location that can be reached by the aimer 426. In yet still other cases, the surgical controller 418 may generate a simulated fluoroscopic images from the three-dimensional bone model, and project thereon a Bernard & Hertel Quadrant or grid. The surgeon may then select the revised-tunnel entry 1306 with the additional guidance provided by the Bernard & Hertel Quadrant.

Figure 14:
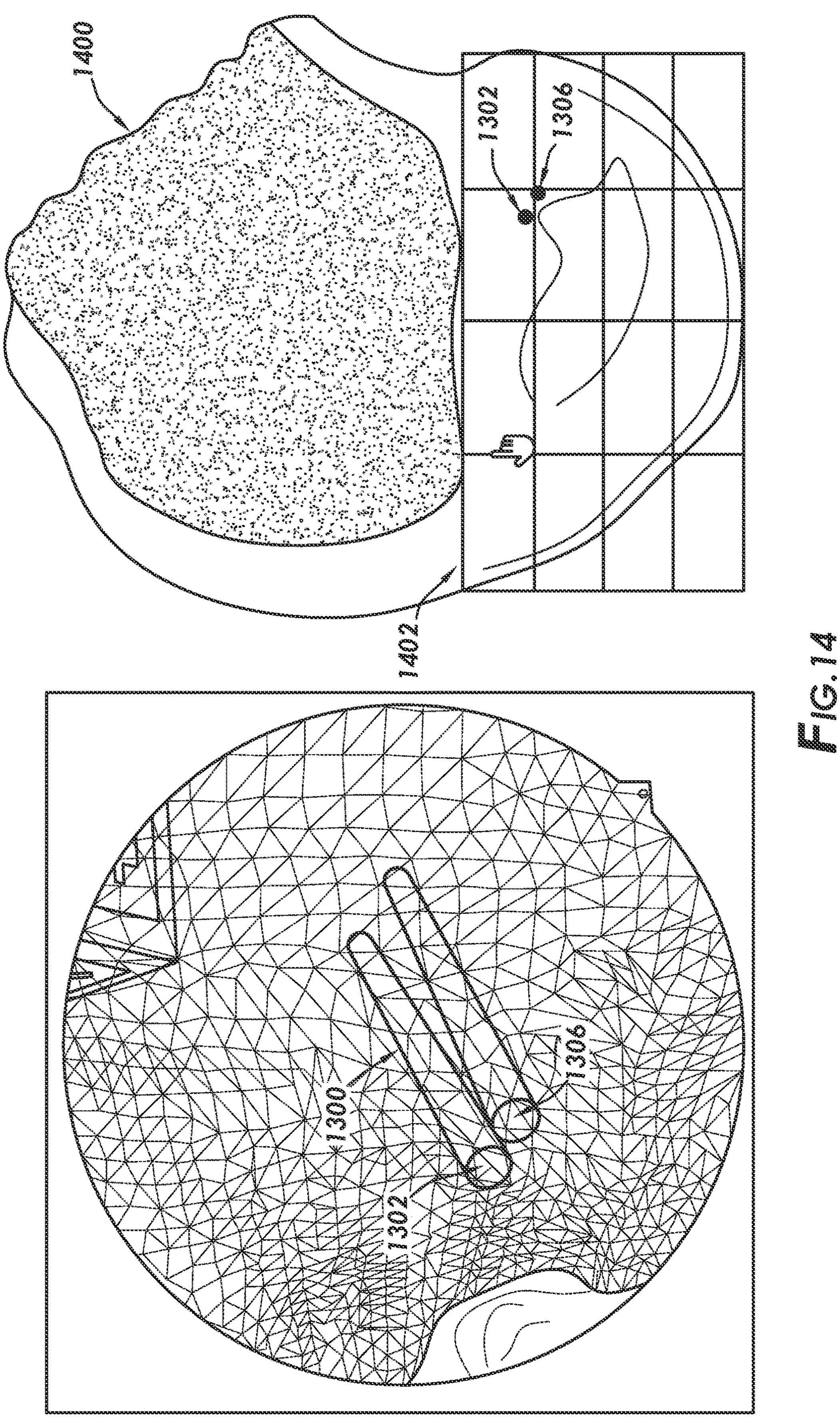
FIG. 14 is an example video display showing planning for intraoperative changes to the tunnel path, in accordance with at least some embodiments.

FIG. 14 is an example video display showing planning for changes to the tunnel path. The display may be shown, for example, on the display device 414 (FIG. 4) associated with the device cart 402 (FIG. 4), or any other suitable location. In particular, FIG. 14 shows, on the left half, a portion of the bone in the video images as captured by the arthroscope 408 (FIG. 4) overlaid with the mesh model of the three-dimensional bone model bone and a depiction of the previously selected planned-tunnel path 1300. On the right side, FIG. 14 shows an example virtual fluoroscopic image 1400 having a Bernard & Hertel Quadrant 1402 overlaid thereon, with the virtual fluoroscopic image created by rending the three-dimensional bone model in a partially transparent form. Alternatively, the virtual fluoroscopic image 1400 may be created as a cross-sectional rendering of the three-dimensional bone model viewed from a medial location toward the lateral side, and with the cut plane for the cross-section through the middle of the intercondylar notch.

In the example systems and methods illustrated by FIG. 14, selection of the revised-tunnel entry 1306 may be guided and/or informed by the virtual fluoroscopic image 1400 and Berndard & Hertel Quadrant 1402. In particular, proposed locations for the revised-tunnel entry 1306 may be displayed in the left half of the display as an overlay on the bone in the video images, and simultaneously displayed on the right half within the Bernard & Hertel Quadrant 1402. For example, the surgeon may provide the proposed revised-tunnel entry 1306 using the touch probe 504 (FIG. 5) or the aimer 426 (FIG. 4). Continuing the description assuming the touch probe 504 is used, as the surgeon moves the touch probe 504 within the view of the arthroscope 408 (FIG. 4), the location of the revised-tunnel entry 1306 is not only visible in relation to the bone within the video images, but also the location of the revised-tunnel entry 1306 is shown on the Bernard & Hertel Quadrant 1402. The surgeon may thus select the revised-tunnel entry 1306 based on the tissues and structures visible in the video images and the additional information provided by the location with the Bernard & Hertel Quadrant 1402. The final revised-entry location 1306 may be conveyed to the surgical controller 418 in any suitable form, such as having the touch probe 504 dwell for a predetermined period of time with the distal end of the touch probe abutting the desired location, or the final selection may be conveyed in other forms (e.g., interaction with a keyboard, a portable tablet device, or a voice command).

Returning to FIG. 13. In many cases, creating a revised-tunnel path involves selecting the revised-tunnel entry 1306, and the other features of the tunnel remain unchanged, such as the tunnel exit location. However, in some cases, and as illustrated in FIG. 13, the surgeon may change both the tunnel entry location and the tunnel exit location. Thus, in yet still further examples, the surgeon may provide the surgical controller 418 (FIG. 4), and thus the surgical controller 418 may receive, a revised-tunnel exit location or just revised-tunnel exit 1308. Providing the revised-tunnel exit 1308 may comprise the surgeon touching the proposed location on the bone shown in the video images with a tracked tool, such as the touch probe 504 (FIG. 5). In various examples, with the revised-tunnel entry 1306 and optionally the revised-tunnel exit 1308, the surgical controller calculates a revised-tunnel path 1310 through the bone of the patient, and displays the revised-tunnel path 1310 on the display device as shown in FIG. 13.

Further in example cases, the surgical controller 418 (FIG. 4) provides information to the surgeon regarding the relationship between the planned-tunnel path 1300 and the revised-tunnel path 1310. In particular, the example video display of FIG. 13 further includes, in the lower right corner, various parameters to help the surgeon assess the viability of the newly created revised-tunnel path 130. For example, the surgical controller 418 may calculate and provide a value indicative of overlap of the planned-tunnel path 1300 and the revised-tunnel path 1310, and the surgical controller 418 may display a visual representation of the value indicative of overlap. In the example of FIG. 13, the visual representation of the value indicative of overlap is a numerical value shown as a percentage (e.g., here 3%). The overlap as a percentage conceptually may span from 0% to slightly less than 100%, as at 100% overlap the revised-tunnel path and the planned-tunnel path would be the same. In some cases, the surgical controller 418 calculates the value indicative of overlap as a percentage taking into account the expected tunnel diameters. If any portion of the planned-tunnel path 1300 intersects any portion of the revised-tunnel path 1310, then that intersection is considered overlap. In other cases, the overlap may be calculated with respect to a planned pilot tunnel and a revised pilot tunnel. The example planned-tunnel path 1300 and revised-tunnel path 1310 of FIG. 13 were selected to have sufficient separation to be visible and distinguishable in the view of FIG. 13; however, in practice the locational change as between the planned-tunnel path 1300 and the revised-tunnel path 1310 may be slight, and thus have significant overlap taking into account the expected diameter of the tunnel path.

Still considering information provided to the surgeon regarding the planned-tunnel path 1300 and the revised-tunnel path 1310, in yet still further examples the surgical controller 418 (FIG. 4) may calculate and provide an entry-location offset as between the planned-tunnel entry 1302 and the revised-tunnel entry 1306, and the surgical controller 418 may display a visual representation of the offset. In the example of FIG. 13, the visual representation of the offset is a numerical value shown in a measurement unit (e.g., millimeters). The surgical controller 418 may also calculate and provide an exit-location offset between the planned-tunnel exit 1304 and the revised-tunnel exit 1308, and the surgical controller 418 may display a visual representation of the offset in the measurement unit. In the example of FIG. 13, the entry offset is shown as 9 mm, and the exit offset is shown as 17 mm. Again, the example planned-tunnel path 1300 and revised-tunnel path 1310 of FIG. 13 were selected to have sufficient separation to be visible and distinguishable in the view of FIG. 13; however, in practice the locational change as between the planned-tunnel path 1300 and the revised-tunnel path 1310 may be slight, and thus have smaller offsets. In many cases the revised-tunnel exit will be identical to the planned-tunnel exit, and in such cases the exit offset will be zero.

Still considering information provided to the surgeon regarding the planned-tunnel path 1300 and the revised-tunnel path 1310, in yet still further examples the surgical controller 418 (FIG. 4) may calculate and provide a value indicative of back wall blowout. The value of indicative of back wall blowout of FIG. 13 has two example aspects—a quantized blowout potential (e.g., low, medium, and high), and a numerical value indicative of back wall blowout potential. In example cases, the numerical value indicative of back wall blowout potential may be a distance, calculated by the surgical controller 418, as between the expected outside diameter of the revised-tunnel path 1310 and the outside surface of the bone of the three-dimensional bone model. More particularly still, in example cases the numerical value indicative of back wall blowout is the calculated shortest distance between the expected inside diameter of the revised-tunnel path and the outside surface of the three-dimensional bone model. In some cases, quantized blowout potential is related to the numerical value indicative back wall blowout potential, for example: "low" blowout potential may be displayed when the shortest distance between the expected inside diameter of the revised-tunnel path and the outside surface of the three-dimensional bone model is 8 mm or more; "medium" blowout potential may be displayed when the shortest distance between the expected inside diameter of the revised-tunnel path and the outside surface of the three-dimensional bone model is between 4 and 8 mm; and "high" blowout potential may be displayed when the shortest distance between the inside diameter of the revised-tunnel path and the outside surface of the three-dimensional bone model is 4 mm or less. In many cases the tunnel path through bone will have a counterbore associated on the intercondylar notch side of the tunnel, though the counterbore aspects are not shown in FIG. 13. It follows that the counterbore portion of the tunnel may have a greater inside diameter than the tunnel near the exit location, and in example case the surgical controller 418 considers the expected inside diameter of the counterbore when calculating the values indicative of back wall blowout potential.

Regardless of the precise information provided to the surgeon regarding the relationship between the planned-tunnel path 1300 and the revised-tunnel path 1310, if the surgeon so elects based on the provided information, the revised-tunnel path 1310 may be scrapped and selecting a revised-tunnel entry may begin anew. The specification continues with the assumption that the surgeon selected a revised-tunnel path 1310 for use; however, it is not necessary that a revised-tunnel path 1310 be selected in every case, and thus the continued description based on the revised-tunnel path 1310 shall not be read as limitation. The specification now turns to creation of the tunnel in accordance with various examples.

Tunnel Creation

With the revised-tunnel path 1310 selected, the next step in the example method is creation of the actual tunnel. In most cases, creating the tunnel is a multistep process involving drilling an initial or pilot tunnel using a drill wire (e.g., drill wire 424 (FIG. 4)), and then using the drill wire as guide wire for one or more reamers to increase the diameter of the pilot tunnel to form the full-diameter actual tunnel though the bone. In some cases the actual tunnel has a counterbore associated with the intercondylar notch to accommodate the width of the autograft, and in such cases an additional reamer may be used to create the counterbore.

Figure 15:
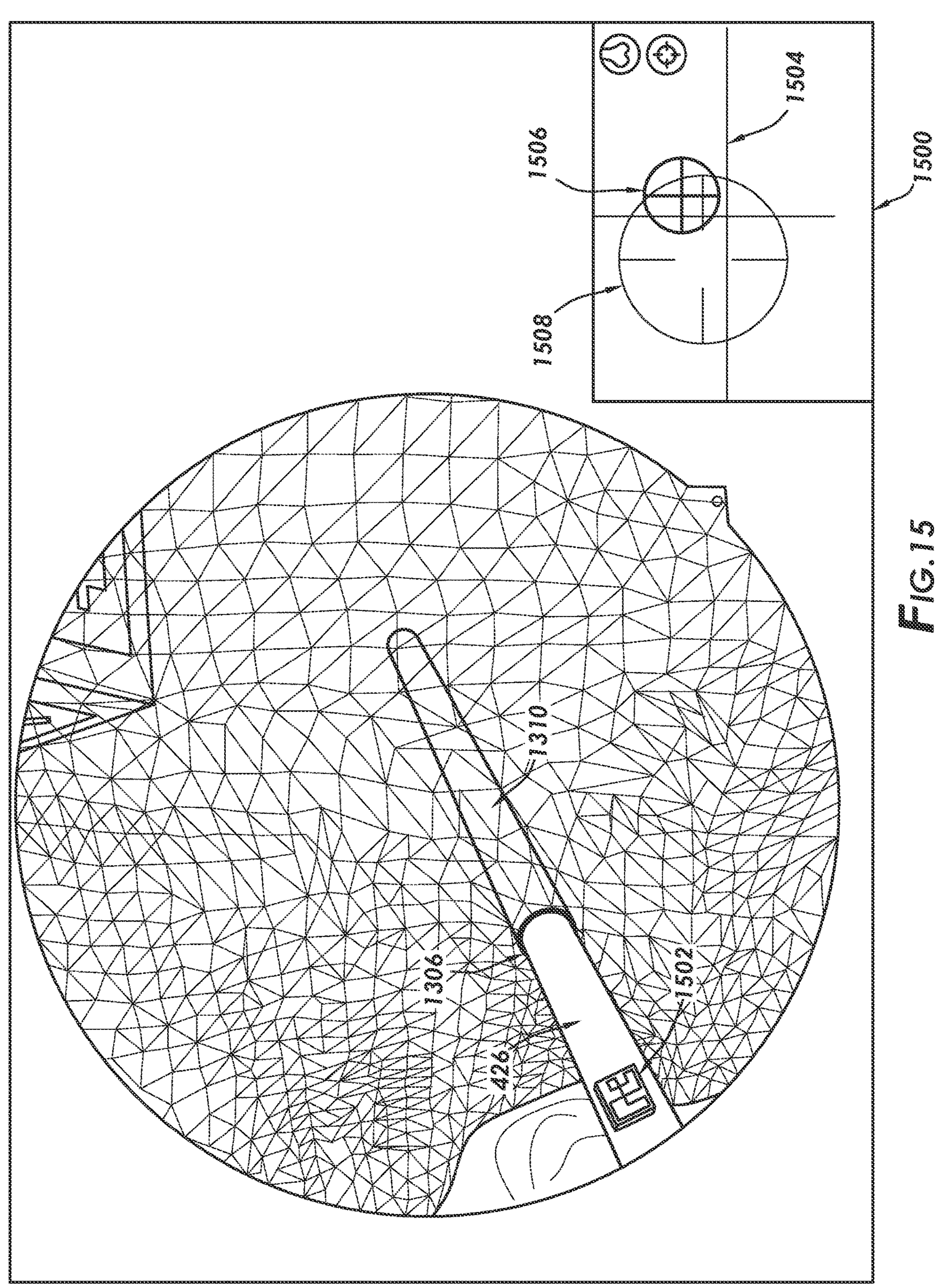
FIG. 15 is an example video display showing computer guidance for placement of a pilot tunnel, in accordance with at least some embodiments.

FIG. 15 is an example video display showing computer guidance for placement of a pilot tunnel. The display may be shown, for example, on the display device 414 (FIG. 4) associated with the device cart 402 (FIG. 4), or any other suitable location. In particular, FIG. 15 shows, in the main portion of the display, a portion of the bone in the video images as captured by the arthroscope 408 (FIG. 4) overlaid with the mesh model of the three-dimensional bone model, a depiction the revised-tunnel path 1310, and the distal end of the example aimer 426. In the lower right corner, FIG. 15 shows an example graphic 1500 that shows the relative locations of the longitudinal central axis of the aimer 426 (which longitudinal central axis corresponds to the drill axis for the drill wire 424 (FIG. 4)) and the longitudinal central axis of the revised-tunnel path 1310.

Referring initially to the aimer 426, the portion of the aimer 426 visible in the view captured by the arthroscope 408 (FIG. 4) includes a tube having a throughbore, and the tube and throughbore define a longitudinal central axis. In example cases the surgeon uses the aimer 426 to hold and guide the drill wire 424 (FIG. 4). Inasmuch as the drill wire 424 may have an outside diameter on the order of about 2.4 mm, the aimer 426 is selected to have an inside diameter to create a slip fit with the drill wire such that longitudinal central axis of aimer 426 is coaxial with the longitudinal central axis of the drill wire 424. Moreover, the portion of the aimer 426 visible in the video images captured by the arthroscope includes an aimer fiducial 1502. Based on the video images, the surgical controller 418 may "see" the aimer fiducial 1502, and thus calculate both the location of the distal end of the aimer 426 and the orientation of the longitudinal central axis of the aimer 426 and drill wire 424, with the locations and orientations thus known in the three-dimensional coordinate space of the view captured by the arthroscope 408.

During the initial placement of the aimer 426, the surgeon may rely upon viewing the relative locations of the aimer 426 and the revised-tunnel path 1310 in the video images. However, for fine alignment of the aimer 426 with the revised-tunnel entry 1306, and alignment of the longitudinal central axis of the aimer 426 with the longitudinal central axis of the revised-tunnel path 1310, in example cases surgeon may rely upon the graphic 1500 generated and shown by the surgical controller 418 (FIG. 4). In particular, in accordance with example systems the surgical controller 418, receiving the video images capture by the arthroscope 408 (FIG. 4) and camera head 410 (FIG. 4), tracks location of the distal end of the aimer 426 relative to the revised-tunnel entry 1306, and displays the graphic 1500 on the display device that shows the relative locations of the revised-tunnel entry 1306 and the distal end of the aimer 426.

In particular, in the lower right corner of the example display is the graphic 1500 including a tunnel-path target 1504 representing the revised-tunnel entry 1306 and illustratively shown as an extended length crosshair. Further in the example graphic 1500 is a distal-end target 1506 representing the position of the distal end of the aimer 426 and illustratively shown as a crosshair embedded within a smaller circle. In example systems and methods, the surgical controller 418 displays the tunnel-path target 1504 as fixed in place on the display device, and further displays the distal-end target 1506 at a variable location to depict the relative positioning of the distal end of the aimer 426 and the revised-tunnel entry 1306. The example video display of FIG. 15 may be shown on a display device having a size (e.g., measured diagonally) of 120 centimeters or more, while the relative spacing between the distal end of the aimer 426 and the revised-tunnel entry 1306 may be just a few centimeters. Thus, the relative locations shown by the tunnel-path target 1504 and the distal-end target 1506 may include a scale factor to provide scaled visual feedback to the surgeon. The goal of the surgeon is to place the distal-end target 1506 aligned with the tunnel-path target 1504 before beginning drilling of the pilot tunnel using the drill wire 424 (FIG. 4). The drill wire 424 may be disposed within the aimer 426 during the alignment process, or the surgeon may align the aimer 426 prior to telescoping the drill wire 424 into the aimer 426.

There are at least two alignments for the surgeon to consider when placing the aimer 426 for drilling of the pilot tunnel: 1) having the actual tunnel entry location close to or aligned with the revised-tunnel entry 1306; and 2) having the longitudinal central axis of the pilot tunnel close to or coaxial with the longitudinal central axis of the revised-tunnel path 1310. Placing the distal-end target 1506 closely aligned with the tunnel-path target 1504 only addresses the first alignment consideration. The distal-end target 1506 may be precisely aligned with the tunnel-path target 1504, yet if the pilot tunnel was drilled the tunnel direction could differ substantially from the revised-tunnel path 1310. In order to enable better axial alignment in accordance with further examples, the surgical controller 418, still receiving the video images capture by the arthroscope 408 (FIG. 4) and camera head 410 (FIG. 4), tracks the orientation of the longitudinal central axis of the aimer 426 relative to the longitudinal central axis of the revised-tunnel path 1310, and displays a graphic on the display device that shows the relative orientations of the central axes.

Again referring to the graphic 1500 in the lower right corner, in example systems and methods the surgical controller 418 (FIG. 4) further generates and displays a proximal-end target 1508 representative of a proximal portion the aimer 426 and illustratively shown as a partial crosshair embedded within a larger circle. In example systems and methods, the surgical controller 418 displays the proximal-end target 1508 at a variable location relative to distal-end target 1506 to show the orientation of the longitudinal central axis of the aimer 426 relative to the longitudinal central axis of the revised-tunnel path 1310. That is, in the graphic 1500 the longitudinal central axis of the revised-tunnel path 1310 may be considered to be perpendicular to the front face of the display device 414 (FIG. 4) and disposed at the intersection or center of the tunnel-path target 1504. The longitudinal central axis of the aimer 426 may be considered to be a line extending between the centers of the proximal-end target 1508 and the distal-end target 1506. The goal of the surgeon is to align the proximal-end target 1508 with the distal-end target 1506, and have the aligned crosshairs 1508/1506 aligned with the tunnel-entry target 1504. When all the crosshairs are aligned, the longitudinal central axis of the aimer 426, the drill wire 424 (FIG. 4) within the aimer 426, and the revised-tunnel path 1310 should be coaxial.

The discussion with respect to FIG. 15 and the graphic 1500 assumed use of the aimer 426 to locate the drill wire 424 (FIG. 4) prior to drilling the pilot hole. Whether or not the drill wire is disposed within the aimer 426 during the alignment process, the longitudinal central axis of the aimer 426 nevertheless represents the expected drill axis once drilling of the pilot tunnel begins. In other cases the aimer 426 may be omitted, and the drill wire 424 itself may be tracked. That is, the drill wire 424 may include a wire fiducial having one more machine readable patterns from which the surgical controller 418 can determine the location of the distal end of the drill wire 424 and the orientation of the longitudinal central axis of the drill wire (at least proximate to the bone within the surgical site). Thus, the discussion to this point assuming use of the aimer 426 as the mechanism for enabling placement and orientation of the drill wire prior to drilling shall not be read as limitation of the claims.

Once the aimer 426 is aligned with the revised-tunnel path 1310, drilling of the pilot tunnel commences. If the drill wire 424 (FIG. 4) is not already telescoped within the aimer 426, the surgeon telescopes the drill wire 424 within the aimer 426. Drilling may involve the surgeon holding the aimer 426 in the desired orientation as shown by the graphic 1500, and providing rotational energy to the drill wire 424, such as by an external drill assembly. Once the drill wire enters the bone, the drill wire 424 drills through the bone in a straight line, and ultimately exits the bone on the far side. For an inside-out procedure, the drill wire also exits the skin on the outside portion of the leg. Once the drill wire 424 completes the pilot tunnel, with the aimer 426 still telescoped over the drill wire 424, placement of the pilot tunnel relative to the revised-tunnel path 1310 may be analyzed.

Tunnel Placement Analysis

In accordance with example methods and systems, prior to using the reamer(s) to create the full diameter tunnel through the bone, the surgical controller 418 (FIG. 4) may provide information to the surgeon regarding the relationship between the pilot tunnel and the revised-tunnel path 1310 to enable the surgeon to determine whether the pilot tunnel should be used as the guide to create the actual tunnel through the bone.

Figure 16:
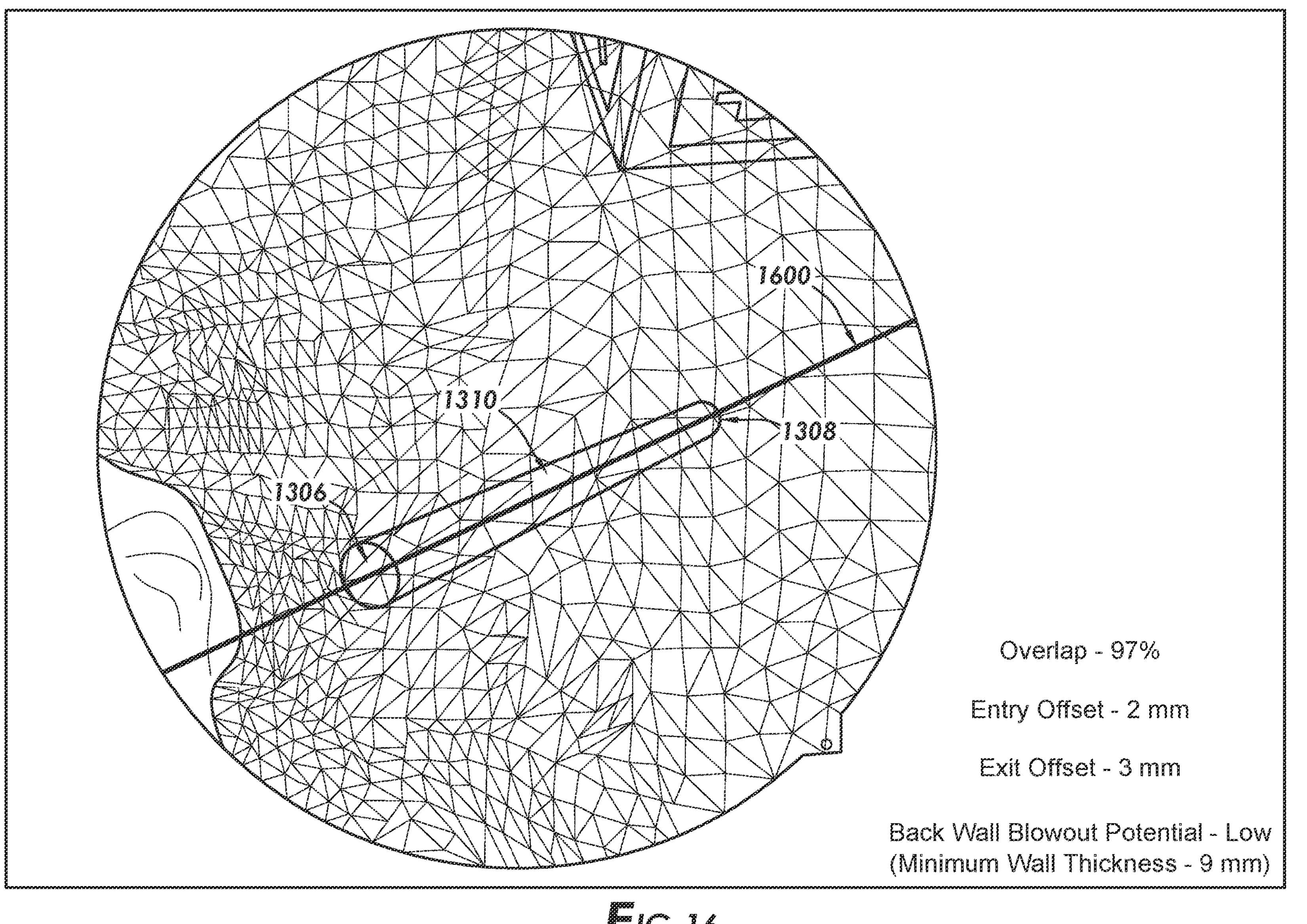
FIG. 16 is an example video display showing intraoperative analysis of the pilot tunnel path relative to the revised-tunnel path, in accordance with at least some embodiments.

FIG. 16 is an example video display showing intraoperative analysis for the pilot tunnel path relative to the revised-tunnel path. The display may be shown, for example, on the display device 414 (FIG. 4) associated with the device cart 402 (FIG. 4), or any other suitable location. In particular, FIG. 16 shows a portion of the bone in the video images as captured by the arthroscope 408 (FIG. 4) overlaid with the mesh model of the three-dimensional bone model, the revised-tunnel path 1310 comprising a revised-tunnel entry 1306 and the revised-tunnel exit 1308, and an overlay showing captured and calculated longitudinal central axis 1600 of the pilot tunnel. The entry for the pilot tunnel may be visible in practice, but is not shown in FIG. 16 so as not to further complicate the figure. The example video display of FIG. 16 further includes, in the lower right corner, various parameters to help the surgeon assess the viability of the pilot tunnel relative to the revised-tunnel path 1310. For example, the surgical controller 418 may calculate and provide a value indicative of overlap of a tunnel along the path of the pilot tunnel relative to the revised-tunnel path 1310, and the surgical controller 418 may display a visual representation of the value indicative of overlap. In the example of FIG. 16, the visual representation of the value indicative of overlap is a numerical value shown as a percentage (e.g., here 97%). The overlap as a percentage conceptually may span from 0% to 100%, with 0% being a complete miss, and 100% meaning the longitudinal central axis 1600 of the pilot tunnel is coaxial with the longitudinal central axis of the revised-tunnel path 1310. As before, the surgical controller 418 calculates the value indicative of overlap as a percentage taking into account the expected tunnel diameters—if any portion of the expected tunnel diameters intersect any portion of the revised-tunnel path 1310, then that intersection is considered overlap. Alternatively, the surgical controller 418 may calculate the value indicative of overlap based on the pilot tunnel and a pilot tunnel that would create the revised-tunnel path 1310.

Still considering information provided to the surgeon regarding the relationship of the expected tunnel along the pilot tunnel and the revised-tunnel path 1310, in yet still further examples the surgical controller 418 (FIG. 4) may calculate and provide an entry-location offset as between the pilot tunnel and the revised-tunnel entry 1306, and the surgical controller 418 may display a visual representation of the offset. In the example of FIG. 16, the visual representation of the offset is a numerical value shown in the measurement unit. The surgical controller 418 may also calculate and provide an exit-location offset between the pilot tunnel and the revised-tunnel exit 1308, and the surgical controller 418 may display a visual representation of the offset in the measurement unit. In the example of FIG. 16, the entry offset is shown as 2 mm, and the exit offset is shown as 3 mm. The example offsets of 2 mm and 3 mm may show that the surgeon was unable to hold the aimer 426 (FIG. 4) precisely at the desired location when drilling began, and/or the surgeon was unable to hold the longitudinal central axis of the aimer 426 coaxial with the longitudinal central axis of the revised-tunnel path 1310. Nevertheless, offsets of 2 mm and 3 mm may be sufficient in view of related-art tunnel placement errors on the order of 8.3 to 13.9 mm.

Still considering information provided to the surgeon regarding the pilot tunnel relative to the revised-tunnel path 1310, in yet still further examples the surgical controller 418 (FIG. 4) may calculate and provide a value indicative of back wall blowout. As with respect to intraoperative changes to create the revised-tunnel path 1310, the value of indicative of back wall blowout of FIG. 16 has two example aspects—a quantized blowout potential (e.g., low, medium, and high), and a numerical value indicative of back wall blowout potential. The numerical value indicative of back wall blowout potential again may be a distance, calculated by the surgical controller 418, as between the expected outside diameter of tunnel created along the pilot tunnel and the outside surface of the bone of the three-dimensional bone model. More particularly still, in example cases the numerical value indicative of back wall blowout potential is calculated as the shortest distance between the expected inside diameter of a tunnel created along the pilot tunnel and the outside surface of the three-dimensional bone model. Again, the quantized blowout potential may be related to the numerical value indicative back wall blowout potential, for example: "low" blowout potential may be displayed when the shortest distance between the expected inside diameter of tunnel created along the pilot tunnel and the outside surface of the three-dimensional bone model is 8 mm or more; "medium" blowout potential may be displayed when the shortest distance is between 4 and 8 mm; and "high" blowout potential may be displayed when the shortest distance is 4 mm or less.

Regardless of the precise information provided to the surgeon regarding the relationship between the expected inside diameter of a tunnel created along the pilot tunnel and the revised-tunnel path 1310, if the surgeon so elects based on the provided information, the pilot tunnel may be abandoned and a new pilot tunnel drilled using the procedures discussed above. If the second or subsequent pilot tunnel meets with the surgeons approval, the example methods proceed to using reamer(s) to create the full-diameter tunnel through bone along the tunnel path, including a counterbore on the intercondylar side of the femur.

SOFTWARE AND HARDWARE

Figure 17:
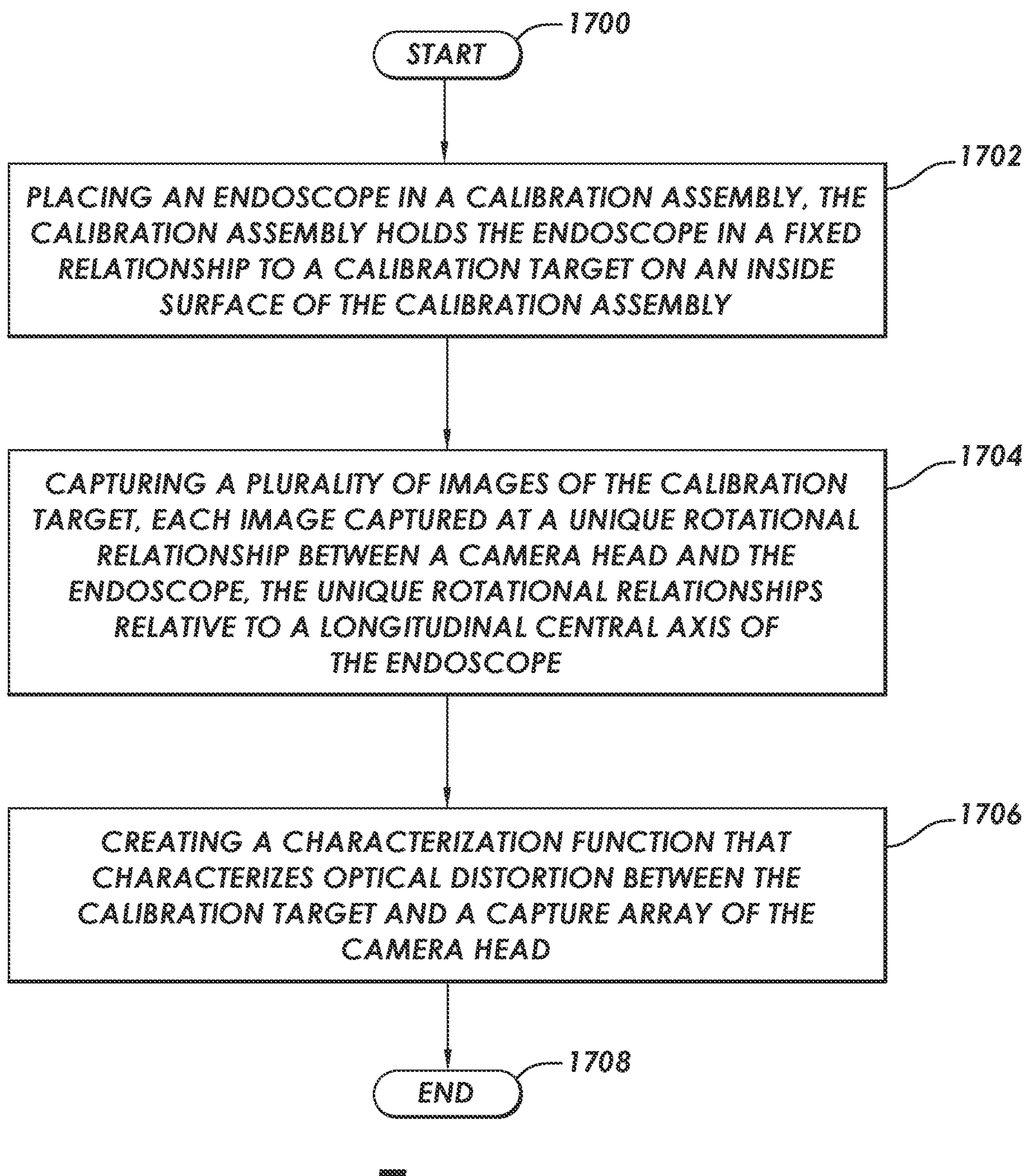
FIG. 17 shows a method of calibrating an endoscopic optical system, in accordance with at least some embodiments.

FIG. 17 shows a method of calibrating an endoscopic optical system, such as an arthroscope and attached camera head, in accordance with at least some embodiments. In particular, the method starts (block 1700) and may comprise: placing an endoscope in a calibration assembly, the calibration assembly holds the endoscope in a fixed relationship to a calibration target on an inside surface of the calibration assembly (block 1702); capturing a plurality of images of the calibration target, each image captured at a unique rotational relationship between a camera head and the endoscope, the unique rotational relationships relative to a longitudinal central axis of the endoscope (block 1704); and creating a characterization function that characterizes optical distortion between the calibration target and a capture array of the camera head (block 1706). Thereafter, the example method ends (block 1708). Portions of the example method may be implemented by computer instructions executed with the processor of computer system, such as the surgical controller 418 (FIG. 4).

Figure 18:
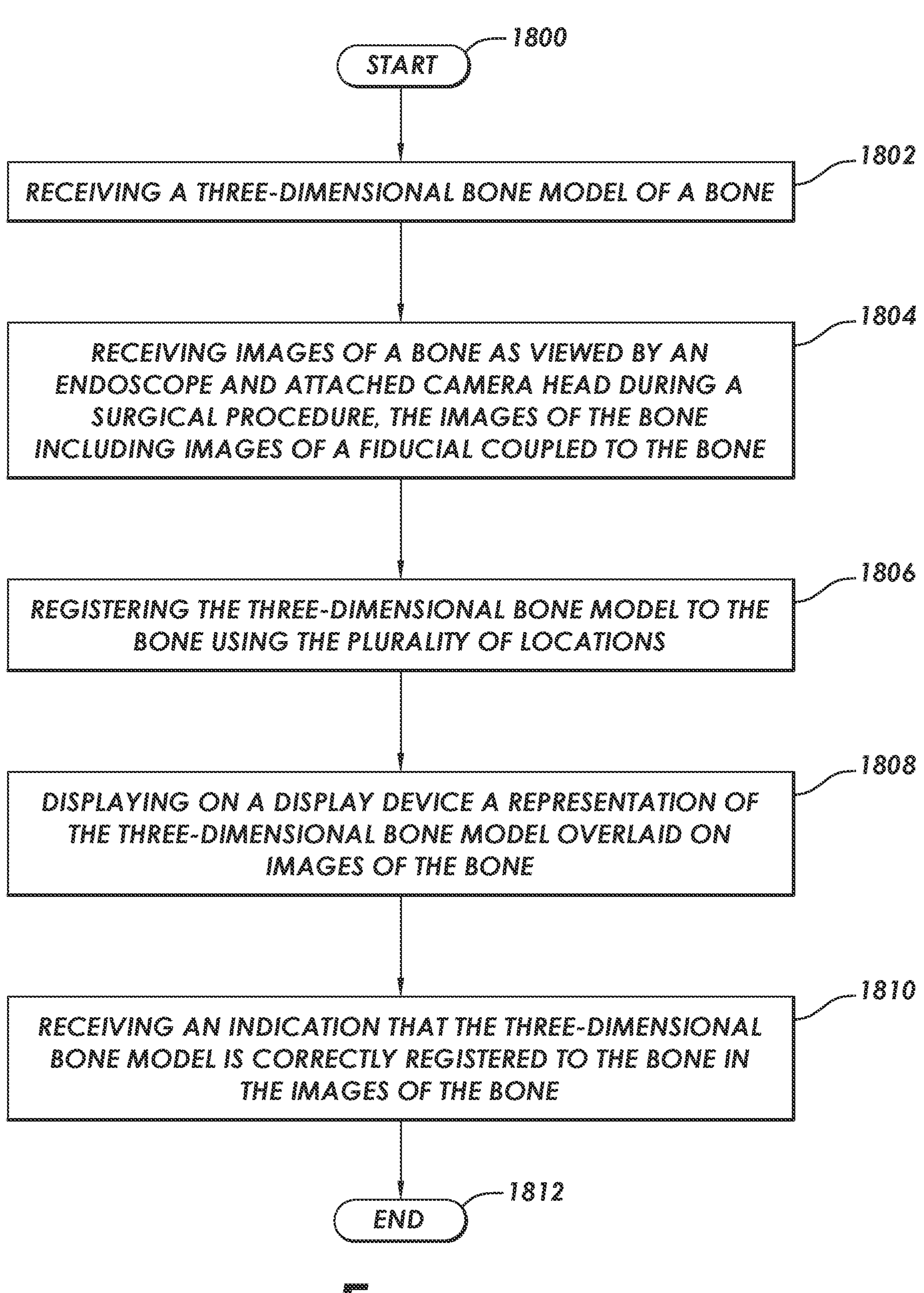
FIG. 18 shows a method of intraoperative verification of registration of a three-dimensional bone model, in accordance with at least some embodiments.

FIG. 18 shows a method of intraoperative verification of registration of a three-dimensional bone model, in accordance with at least some embodiments. In particular, the method starts (block 1800) and comprises: receiving a three-dimensional bone model a bone (block 1802); receiving images of a bone as viewed by an endoscope and attached camera head during a surgical procedure, the images of the bone including images of a fiducial coupled to the bone (block 1804); receiving a plurality of locations of an outer surface of the bone shown in the images of the bone (block 1806); registering the three-dimensional bone model to the bone using the plurality of locations (block 1808); displaying on a display device a representation of the three-dimensional bone model overlaid on images of the bone (block 1810); and receiving an indication that the three-dimensional bone model is correctly registered to the bone in the images of the bone (block 1812). Thereafter, the method ends (block 1812). The example method may be implemented by computer instructions executed with the processor of computer system, such as the surgical controller 418 (FIG. 4).

Figure 19:
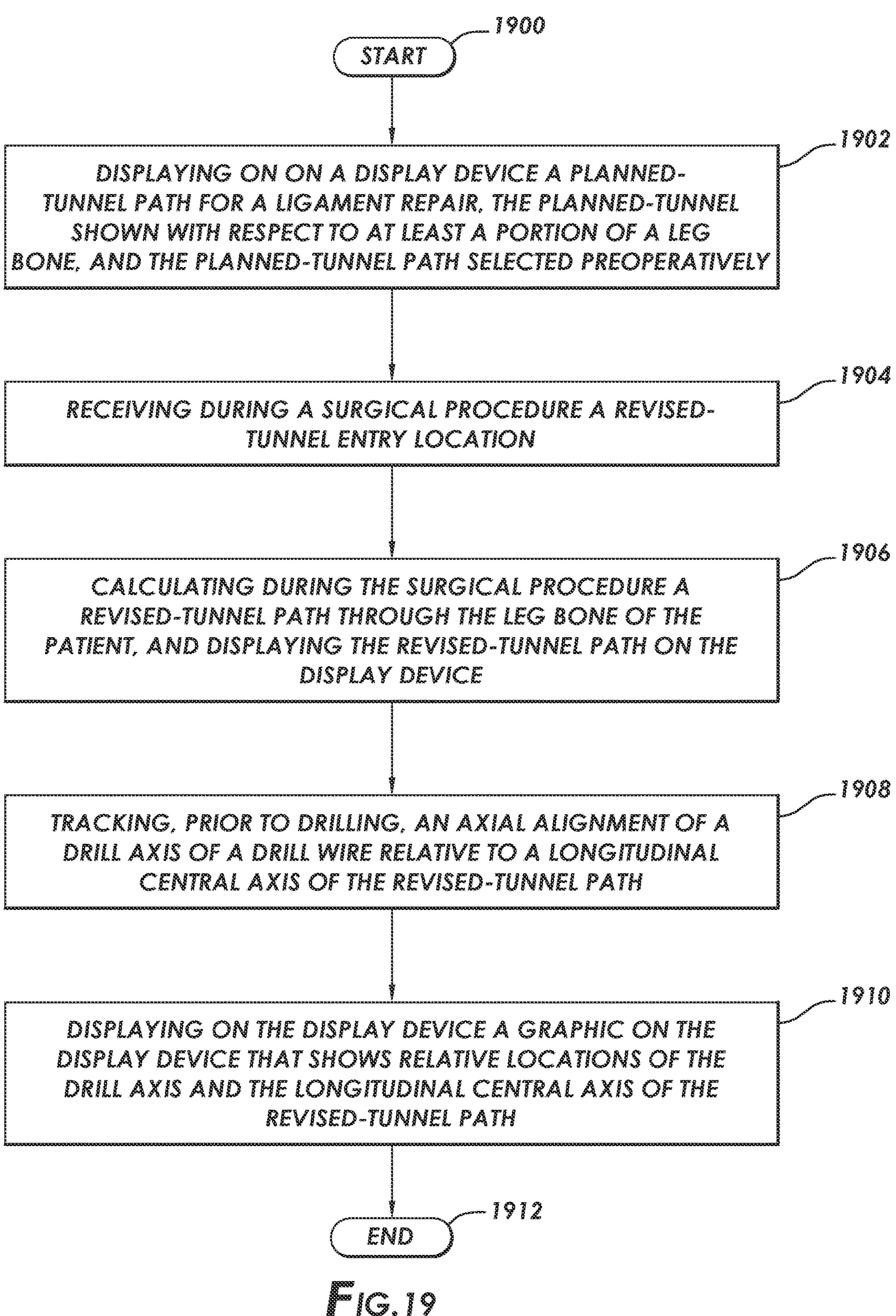
FIG. 19 shows a method of implementing intraoperative tunnel path changes, in accordance with at least some embodiments.

FIG. 19 shows a method of implementing intraoperative tunnel path changes, in accordance with at least some embodiments. In particular, the method starts (block 1900) and comprises: displaying on a display device a planned-tunnel path for a ligament repair, the planned-tunnel path shown with respect to at least a portion of a leg bone, and the planned-tunnel path selected preoperatively (block 1902); receiving during a surgical procedure a revised-tunnel entry location (block 1904); calculating during the surgical procedure a revised-tunnel path through the leg bone of the patient, and displaying the revised-tunnel path on the display device (block 1906); tracking, prior to drilling, an axial alignment of a drill axis of a drill wire relative to a longitudinal central axis of the revised-tunnel path (block 1908); and displaying on the display device a graphic on the display device that shows relative locations of the drill axis and the longitudinal central axis of the revised-tunnel path (block 1910). Thereafter, the method ends (block 1912). The example method may be implemented by computer instructions executed with the processor of computer system, such as the surgical controller 418 (FIG. 4).

Figure 20:
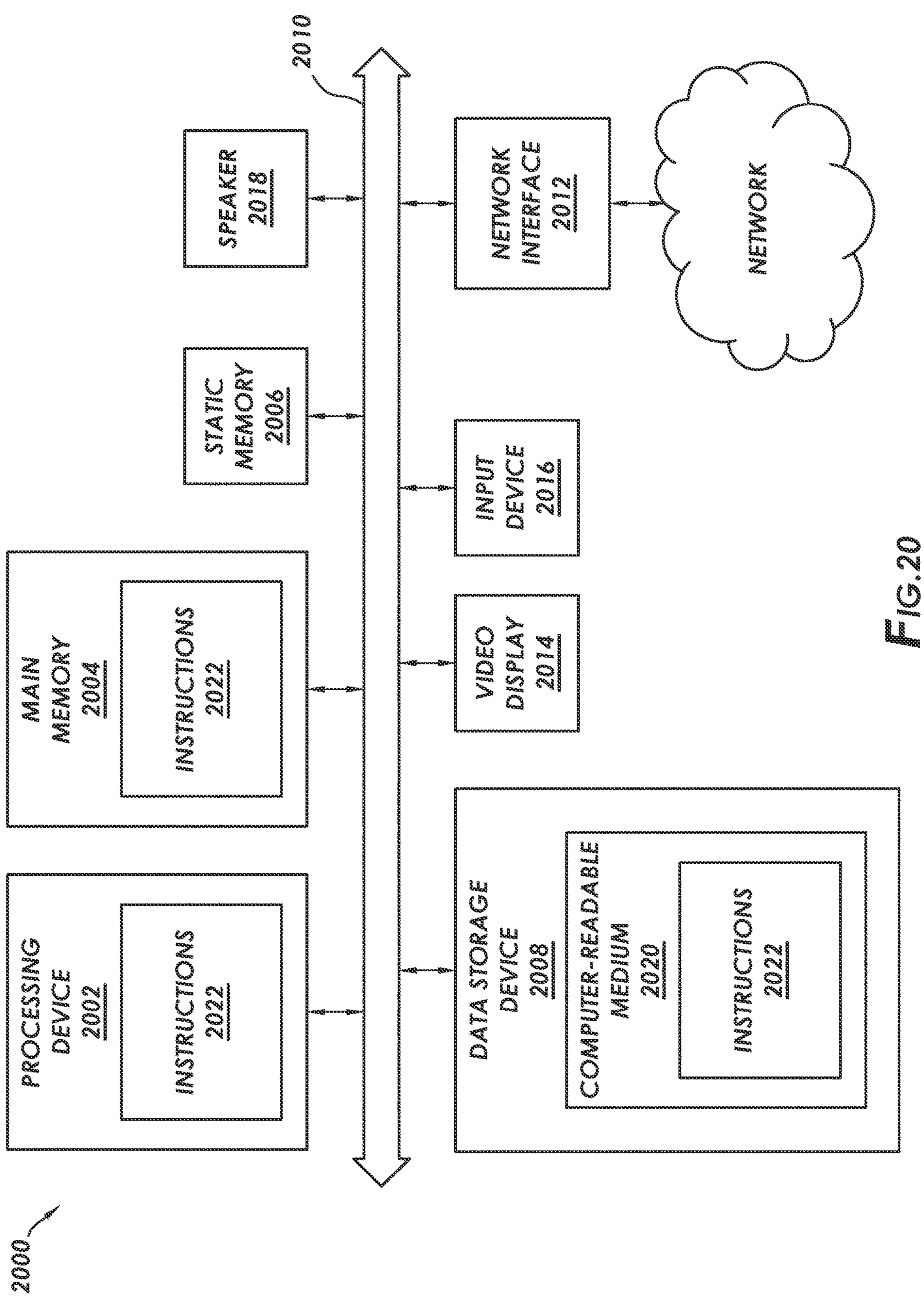
FIG. 20 shows a computer system in accordance with at least some embodiments.

FIG. 20 shows an example computer system 2000. In one example, computer system 2000 may correspond to the surgical controller 418, a tablet device within the surgical room, or any other system that implements any or all the various methods discussed in this specification. The computer system 2000 may be connected (e.g., networked) to other computer systems in a local-area network (LAN), an intranet, and/or an extranet (e.g., device cart 402 network), or at certain times the Internet (e.g., when not in use in a surgical procedure). The computer system 2000 may be a server, a personal computer (PC), a tablet computer or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 2000 includes a processing device 2002, a main memory 2004 (e.g., read-only memory (ROM), flash memory, dynamic random access memory (DRAM) such as synchronous DRAM (SDRAM)), a static memory 2006 (e.g., flash memory, static random access memory (SRAM)), and a data storage device 2008, which communicate with each other via a bus 2010.

Processing device 2002 represents one or more general-purpose processing devices such as a microprocessor, central processing unit, or the like. More particularly, the processing device 2002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 2002 may also be one or more special-purpose processing devices such as an application specific integrated circuit (ASIC), a field programmable gate array (FPGA), a digital signal processor (DSP), network processor, or the like. The processing device 2002 is configured to execute instructions for performing any of the operations and steps discussed herein. Once programmed with specific instructions, the processing device 2002, and thus the entire computer system 2000, becomes a special-purpose device, such as the surgical controller 418.

The computer system 2000 may further include a network interface device 2012 for communicating with any suitable network (e.g., the device cart 402 network). The computer system 2000 also may include a video display 2014 (e.g., display device 414), one or more input devices 2016 (e.g., a microphone, a keyboard, and/or a mouse), and one or more speakers 2018. In one illustrative example, the video display 2014 and the input device(s) 2016 may be combined into a single component or device (e.g., an LCD touch screen).

The data storage device 2008 may include a computer-readable storage medium 2020 on which the instructions 2022 (e.g., implementing any methods and any functions performed by any device and/or component depicted described herein) embodying any one or more of the methodologies or functions described herein is stored. The instructions 2022 may also reside, completely or at least partially, within the main memory 2004 and/or within the processing device 2002 during execution thereof by the computer system 2000. As such, the main memory 2004 and the processing device 2002 also constitute computer-readable media. In certain cases, the instructions 2022 may further be transmitted or received over a network via the network interface device 2012.

While the computer-readable storage medium 2020 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A calibration assembly for calibrating an endoscopic optical system, the calibration assembly comprising:

a lower housing defining a calibration surface;

an upper housing defining a vessel and a tube extending away from the vessel, wherein the tube is integrally formed with the vessel of the upper housing, wherein the vessel and the lower housing together define an internal volume, and wherein the tube does not extend into the internal volume;

a calibration target disposed on the calibration surface;

a wall of the vessel defining an aperture into the vessel, wherein the aperture defines a central axis that intersects the calibration target; and an axial and rotational retention surface defined by a distal end of the tube, wherein the axial and rotational retention surface extends radially outward from the distal end of the tube and is a predetermined distance from the calibration target measured along the central axis of the aperture.

2. The calibration assembly of claim 1, wherein the axial and rotational retention surface further comprises a clip configured to hold a light post of an endoscope, wherein the clip is disposed at and extends from the distal end of the tube.

3. The calibration assembly of claim 1 wherein the calibration surface is planar.

4. The calibration assembly of claim 1 wherein the calibration surface defines a first portion that defines a first plane, and a second portion that defines a second plane, and wherein the first plane and the second plane are non-planar.

5. The calibration assembly of claim 1 wherein the central axis of the aperture intersects a center of the calibration target.

6. The calibration assembly of claim 1 wherein the central axis of the aperture forms an acute angle with a vector normal to the calibration surface, the acute angle is non-zero.

7. The calibration assembly of claim 1, wherein:

the calibration surface is planar and defines a first plane;

the lower housing comprises a stand having a lower end that defines a second plane that is not parallel with the first plane; and a longitudinal central axis of the tube intersects the calibration surface such that the longitudinal central axis forms an acute angle with the first plane defined by the calibration surface.

8. The calibration assembly of claim 1, wherein the wall of the vessel including the aperture defines a flange at a transition from the tube to the internal volume, and wherein an inside diameter of the flange is less than an inside diameter of the tube.

9. A system for calibrating an endoscopic optical system, the system comprising:

an endoscopic system comprising an endoscope and a camera head coupled to the endoscope, the endoscope defines a longitudinal central axis and a light post;

a calibration assembly comprising:

a lower housing defining a calibration surface;

an upper housing defining a vessel and a tube extending away from the vessel, wherein the tube is integrally formed with the vessel of the upper housing, wherein the vessel and the lower housing together define an internal volume, and wherein the tube does not extend into the internal volume;

a calibration surface defined on an inside surface of the vessel;

a calibration target disposed on the calibration surface;

an aperture defined through a wall of the vessel, and the endoscope telescoped through the tube and the aperture such that the longitudinal central axis intersects the calibration target; and an axial and rotational retention surface that extends radially outward from a distal end of the tube and is configured to hold a distal end of the endoscope a predetermined distance from the calibration target, wherein the calibration assembly is configured to hold the endoscope in a fixed rotational orientation relative to the calibration target.

10. The system of claim 9 wherein the axial and rotational retention surface comprises a notch defining a channel with a closed bottom and an open top, wherein the light post is disposed within the notch, and wherein the notch holds the distal end of the endoscope the predetermined distance from the calibration target, and the notch holds the endoscope in the fixed rotational orientation relative to the calibration target.

11. The system of claim 9, wherein the axial and rotational retention surface comprises a clip coupled to the light post, wherein the clip holds the endoscope in the fixed rotational orientation relative to the calibration target, and wherein the clip is disposed at and extends from the distal end of the tube.

12. The system of claim 9 further comprising at least one selected from a group comprising: water within the internal volume between the distal end of the endoscope and the calibration target; and saline within the internal volume between the distal end of the endoscope and the calibration target.

13. The system of claim 9 wherein the calibration surface is planar.

14. The system of claim 9 wherein the calibration surface defines a first portion that defines a first plane, and a second portion that defines a second plane, and wherein the firs plane and the second plane are non-planar.

15. The system of claim 9 wherein at least one of: the longitudinal central axis of the endoscope intersects a center of the calibration target; and the longitudinal central axis of the endoscope forms an acute angle with a vector normal to the calibration surface, wherein the acute angle is non-zero.

16. The system of claim 9, wherein:

the calibration surface is planar and defines a first plane;

the lower housing comprises a stand having a lower end that defines a second plane that is not parallel with the first plane; and a longitudinal central axis of the tube intersects the calibration surface such that the longitudinal central axis forms an acute angle with the first plane defined by the calibration surface.

17. The system of claim 9, wherein the wall of the vessel including the aperture defines a flange at a transition from the tube to the internal volume, and wherein an inside diameter of the flange is less than an inside diameter of the tube.

* * * * *